United States Patent [19]
Hanson et al.

[11] Patent Number: 6,110,713
[45] Date of Patent: Aug. 29, 2000

[54] **PRODUCTION OF GLUTAMIC ACID AND LYSINE USING AUXOTROPHIC MUTANTS OF *BACILLUS METHANOLICUS***

[75] Inventors: Richard S. Hanson, Wayzata; Michael C. Flickinger, St. Paul; Patricia Olson, Maple Plain; Won Hur, Lauderdale; Nuhza Al-Tahoo, Sherwood; Craig Bremmon, Roseville, all of Minn.

[73] Assignee: Regents of the University of Minnesota, Minneapolis, Minn.

[21] Appl. No.: 08/787,206

[22] Filed: Jan. 22, 1997

Related U.S. Application Data

[63] Continuation of application No. 08/036,187, Mar. 23, 1993, abandoned.

[51] Int. Cl.$^7$ ..................................................... C12P 13/14
[52] U.S. Cl. ........................... 435/110; 435/115; 435/111; 435/172.1; 435/252.1; 435/252.5
[58] Field of Search ..................................... 435/110, 115, 435/111, 106, 252.1, 252.5, 172.1

[56] References Cited

U.S. PATENT DOCUMENTS

| | | | |
|---|---|---|---|
| 3,212,994 | 10/1965 | Kono et al. | 435/111 |
| 3,359,178 | 12/1967 | Tanaka et al. | 435/110 |
| 3,563,857 | 2/1971 | Oki et al. | 435/111 |
| 3,663,370 | 5/1972 | Kono et al. | 435/110 |
| 3,939,042 | 2/1976 | Nakayama et al. | 435/110 |
| 5,250,434 | 10/1993 | Yamada et al. | 435/110 |

FOREIGN PATENT DOCUMENTS

| | | | |
|---|---|---|---|
| 0034837 | 9/1974 | Japan | 435/110 |
| 2048393 | 3/1987 | Japan | 435/110 |
| 0732377 | 5/1980 | U.S.S.R. | 435/110 |
| 0826097 | 12/1959 | United Kingdom | 435/110 |

OTHER PUBLICATIONS

P. J. Large et al., "Microbial Growth on $C_1$ Compounds", *Biochem. J.*, 87, 386–396 (1963).
Large et al., "Production of Amino Acids, Nucleotides and Other Complex Organic Chemicals From Methylotrophs", *Methylotrophy and Biotechnology*, Longman Scientific and Technical, John Wiley and Sons, New York, New York, pp. 146–162 (1988).
Laskin and Lechevalier, *CRC Handbook of Microbiology*, vol. I, CRC Press, pp. 734–735 (1971).
J. D. Linton et al., "The Potential of One–Carbon Compounds as Fermentation Feedstocks", *Microbial Growth on $C_1$ Compounds*, H. W. van Verseveld and J. S. Duine, eds., Martinus Nyhoff, Dordrecht, pp. 263–271 (1987).
S. M. Machlin et al., "Genetic and Physical Analyses of Methylobacterium organophilum XX Genes Encoding Methanol Oxidation", *J. Bacteriol.*, 170, 141–148 (Jan. 1988).
M. Mandel et al., "Use of Ultraviolet Absorbance–Temperature Profile for Determining the Guanine Plus Cytosine Content of DNA", *Methods Enzymol.*, 12, 195–206 (1968).
A. Mimura et al., "Isolation and Characterization of a Gram–positive Methanol Assimilating Bacterium", *J. Ferment. Technol.*, 56, 243–252 (1978).
H. Motoyama et al. "Amino Acid Production from Methanol by Methylobacillus glycogenes Mutants: Isolation of L–Glutamic Acid Hyper–producing Mutants from M. glycogenes Strains, and Derivation of L–Threonine and L–Lysine–producing Mutants from Them", *Biosci. Biotech. Biochem.*, 57, 82–87 (1993).
A. A. Nicholaidis et al., "Isolation of Methane Monooxygenase–Deficient Mutants from Methylosinus trichosporium OB3b Using Dichloromethane", *FEMS Microbiol. Lett.*, 41, 47–52 (1987).
D. N. Nunn et al., "Phenotypic Characterization of 10 Methanol Oxidation Mutant Classes in Methylobacterium sp. Strain AM1", *J. Bacteriol*, 166, 591–597 (1986).
H. J. Rogers et al., "The Isolation and Characterization of Mutants of *Bacillus subtilis* and *Bacillus licheniformis* with Disturbed Morphology and Cell Division", *J. Gen. Microbiol.*, 61, 155–171 (1970).
F. J. Schendel et al., "L–Lysine Production from Methanol at High Cell Densities of MGA3, a Thermophilic Bacillus sp.," Abstract from 1989 ASM Annual Meeting (published Mar. 21, 1989).
F. J. Schendel et al., "L–Lysine Production at 50° C. by Mutants of a Newly Isolated and Characterized Methylotrophic Bacillus sp.", *Appl. Env. Microbiol.*, 56, 963–970, Apr. 1990.
*Program of the 89th Annual Meeting of the American Society for Microbiology*, p. 193 lists the title for the following poster session: No. 0 69, F. J. Schendel et al. "L–Lysine Production from Methanol at High Cell Densities of MGA3, a Thermophilic Bacillus sp." This program was made available to Meeting registrants as of Mar. 21, 1989.
I. Shiio, "Tryptophan, Phenylalanine, and Tyrosine," 188–206 (1986).
R. Simon et al., "A Broad Host Range Mobilization System for in vivo Genetic Engineering: Transposon Mutagenesis in Gram Negative Bacteria", *Bio/Technology*, 1, 784–791 (1983).
B. Snedecor et al., "Thermophilic Mixed Culture of Bacteria Utilizing Methanol for Growth", *Appl. Microbiol.*, 27, 1112–1117 (1974).
O. Tosaka et al., "The Production of L–Lysine by Fermentation", *Trends in Biotechnology*, 1, 70–74 (1983).
O. Tosaka et al., "Lysine," in *Progress in Industrial Microbiology*, 24, K. Aida et al., eds., pp. 152–172 (1986).
R. Whittenbury et al., "Exospores and Cysts Formed by Methane–utilizing Bacteria", *J. Gen. Microbiol.*, 61, 219–226 (1970).
E. Work, "Reaction of Ninhydrin in Acid Solution with Straight–Chain Amino Acids Containing Two Amino Groups and its Aplication to the Estimation of αϵ–Diaminopimelic Acid", *Bioch.*, 67, 416–423 (1957).

*Primary Examiner*—Irene Marx
*Attorney, Agent, or Firm*—Merchant, Gould, Smith, Edell, Welter & Schmidt, P.A.

[57] ABSTRACT

A method of producing glutamic acid by culturing an amino acid auxotroph of a biologically pure strain of *Bacillus methanolicus* which exhibits sustained growth at 50° C. using methanol as a carbon and energy source and requiring vitamin $B_{12}$ and biotin is provided.

9 Claims, 11 Drawing Sheets

PRODUCTION OF GLUTAMIC ACID AND LYSINE USING AUXOTROPHIC MUTANTS OF BACILLUS METHANOLICUS

This is a Continuation of application Ser. No. 08/036,187, filed Mar. 23, 1993, now abandoned.

BACKGROUND OF THE INVENTION

This invention relates to production of amino acids using auxotrophic mutants of Bacillus methanolicus.

Microorganisms that utilize one-carbon compounds more reduced than carbon dioxide (methylotrophs) are diverse and ubiquitous. Anthony, The Biochemistry of Methylotrophs, page 3 (Academic Press, London 1982); Hanson, Adv. Appl. Microbiol., 26: 3 (1980). Those methylotrophic bacteria reported to utilize methane are all gram-negative and nearly all have an obligate requirement for one-carbon compounds as energy sources. Anthony, supra; Whittenburg et al. J. Gen. Microbiol., 61: 219–226 (1970). Bacteria that grow on methanol and methylamines but not methane include several facultative as well as obligate methylotrophs. Anthony, supra; Hanson, supra. All the obligate methylotrophs unable to utilize methane are gram-negative aerobic bacteria. Anthony, supra.; Whittenburg, supra. Of the facultative methylotrophs isolated that utilize methanol, methylamine or both, only a few were gram positive and were assigned to the genera Bacillus, Corynebacterium, Arthrobacter, or Nocardia. Akiba et al, J. Ferment. Technol., 48: 323–328 (1970); Clement et al. Abstracts of the Fifth International Symposium Microbiol. Growth on $C_1$ Compounds, p. 69 (Free Univ. Press, Amsterdam 1986); Hazen et al, Arch. Microbiol., 135: 205–210 (1983); Mimura et al., J. Ferment. Technol., 56: 243–252 (1978).

Some species of facultative gram positive methyltrophs that utilize methanol, methylamine or both have now been classified together and named Bacillus methanolicus. Arfman et al., Int. J. System. Bact., 42: 438 (1992). Strains of Bacillus methanolicus have the following identifying characteristics: (1) cells are rod shaped, non-motile, and gram positive; (2) sporulating cells possess oval spores in a subterminal to central position; (3) growth is obligately aerobic at temperatures between 35 to 60° C. with optimum growth at 55° C.; and (4) all strains exhibit growth on methanol. Other characteristics of Bacillus methanolicus are identified in Arfman et al., cited supra.

Production of single cell protein and selected amino acids by microbial fermentation is known, e.g., U.S. Pat. No. 4,652,527 to Stirling. One amino acid which has been produced on an industrial scale is lysine, see Tosaka et al., Trends in Biotechnology, 1: 70–74 (1983), Tosaka and Takinami, Progress in Industrial Microbiology, Ch. 24, pp. 152–172 (Aida et al., 1986). Another example is glutamic acid which has been produced using bacteria of the genera Corynebacterium, Brevibacterium, Microbacterium, and Arothrobacter by fermentation on molasses and starch hydrozylates. Aspartic acid and alanine are produced by enzymatic means from fumaric acid and ammonia. Bacillus species have been used in fermentation processes to produce amino acids, Tosaka et al., supra.; Tosaka and Takinami, supra. However, to date no production of amino acids using an isolated Bacillus species capable of rapid growth on methanol at temperatures above 50° C. has occurred.

The industrial advantages of a thermophilic methanol utilizing fermentation process at elevated temperatures have been described, Snedecor and Cooney, Appl. Microbiol., 27: 112–1117 (1974). For example, use of elevated temperatures can significantly reduce cooling costs. Use of methanol as a carbon and energy source is cost efficient because of its wide availability and low cost. A methanol utilizing, thermophilic mixed culture that included an endospore-forming species was selected by Snedecor and Cooney; however, Snedecor and Cooney, were unable to isolate a pure culture capable of growth on methanol. It is extremely difficult or impossible to isolate appropriate mutants from mixed or impure cultures.

Large scale production of amino acids including glutamic and aspartic acids is desired for many commercial applications. For example, glutamic acid is used in the production of moisturizers in cosmetics, gelatinizing agents in vegetable oils, for oil dispersion, and as a seasoner for foods. The demand for monosodium glutamate exceeds 300,000 tons per year. L-aspartic acid is used as a flavoring agent and to produce the sweetener Aspartame™. The widespread use of this sweetener has rapidly increased demand for L-aspartic acid.

Accordingly, there is a need for a method of producing amino acids using a type I methylotrophic bacterium of the genus Bacillus which exhibits sustained growth on methanol at a temperature of at 50° C. There is also a need for an inexpensive method of producing an amino acid such as glutamic acid on an industrial scale.

SUMMARY OF THE INVENTION

The invention provides a method and microorganisms for producing glutamic acid. The method involves culturing an auxotroph of the Bacillus methanolicus in media with methanol as a carbon source at a temperature of about 50° C. until glutamate is produced and recovering glutamate from the nutrient media. The method is especially useful to produce glutamate on an industrial scale from an inexpensive and readily available substrate such as methanol.

An auxotroph of Bacillus methanolicus is generated by mutagenesis and selection of amino acid producing strains. Strains of Bacillus methanolicus of the invention have the following characteristics: (1) rod-shaped, non-motile and gram positive; (2) spore forming with spores present at central to subterminal location; (3) obligate aerobic growth at temperatures of about 35 to 60° C. with optimal growth at about 55° C.; (4) exhibits sustained growth and methanol; and (5) utilizes a ribulose monophosphate pathway to convert methanol to carbon dioxide. Auxotroph strains of Bacillus methanolicus can be generated by standard methods of mutagenesis including chemical mutagenesis, UV irradiation, site specific mutagenesis and transposon mediated mutagenesis. Amino acid auxotrophs are identified and can be further selected by resistance to growth inhibition by amino acid analogs such as s-2-aminoethyl-L-cysteine, hydroxylysine, methyllysine and mixtures thereof.

The preferred auxotrophs of the invention are biologically pure cultures of a ribulose monophosphate pathway utilizing auxotroph of a strain having all the identifying characteristics of B. methanolicus and that produces glutamate. The auxotroph exhibits sustained growth at 50° C. in nutrient media comprising methanol as a carbon source and produces glutamate at a concentration of at least about 5 g/l. The auxotroph also requires biotin and vitamin $B_{12}$ as trace supplements. More preferably the auxotroph produces about 5 to 150 g/l glutamate, and most preferably about 50 to 150 g/l glutamate. The auxotroph can also coproduce other amino acids including lysine, aspartic acid, alanine and mixtures thereof.

In the preferred version, glutamate is produced by growth of an amino acid auxotroph of B. methanolicus under fed-batch or semi-continuous culture conditions. A homoserine auxotroph is grown under conditions where threonine, methionine and phosphate are limited. Limitation of threonine after the cell cultures reach sufficient cell density enhances glutamate production. The cultures are grown until glutamate is produced at a concentration at least about 5 g/l or until cell densities are about 20 g dry cell weight per liter or greater.

DETAILED DESCRIPTION OF THE DRAWING

A. Isolation and Characteristics of the Bacillus methanolicus Strains

The methylotrophic bacterium of the present invention is a strain of Bacillus methanolicus, preferably, having the characteristics as set forth in Table I, below.

TABLE I

Characteristics of Some Strains of Bacillus methanolicus

| | |
|---|---|
| Cell shape | rod |
| Gram-reaction | + |
| Endospores | oval |
| Sporangia | swollen |
| Spore localization | subterminal |
| Survival after 10 min. at 80° C. | + |
| Sporulation at 53° C. | - |
| Sporulation at 37° C. | + |
| Motility | - |
| Optimum pH for growth | 7 |
| Optimum temperature for growth | 45–55° C. |
| Vitamin requirements | $B_{12}$, Biotin |
| Carbon and energy sources: | |
| Methanol | ++ |
| Mannitol | ++ |
| Glucose | + |

TABLE I-continued

Characteristics of Some Strains of Bacillus methanolicus

| | |
|---|---|
| Ribose | w |
| Maltose | w |
| Acetate | w |
| Glutamate | w |
| α-Ketoglutarate | w |
| Gas from carbohydrate | - |
| Growth on nutrient agar | w |
| Nitrogen Source: | |
| Ammonium | + |
| Nitrate | - |
| Nitrate reduction | - |
| Nitrate respiration | - |
| Urease | + |
| Catalase | - |
| Hexulose phosphate synthase | + |
| Hydrolysis of: | |
| Gelatin | + |
| Starch | + |
| Casein | - |
| NaCl tolerance | 1% |
| DNA base ratios (moles % G + C) | 44 | w = weak positive; . = not determined.

Other characteristics of strains of bacteria classified as B. methanolicus can be found in Arfman et al., Int. J. Syst. Bact., 42: 439 (1992), which is hereby incorporated by reference. Although fermentation of substrates can vary among the strains as shown by Arfman et al., there are several characteristics that identify a bacterium as a strain of B. methanolicus. These characteristics include: (1) the bacteria are rod shaped, non-motile, and gram positive; (2) the bacteria form spores at a subterminal to central position; (3) growth is obligately aerobic and occurs at temperatures 35–60° C., with optimum growth at 55° C.; (4) growth on methanol is exhibited; and (5) the G/C content is about 44–52%.

Figure 9:
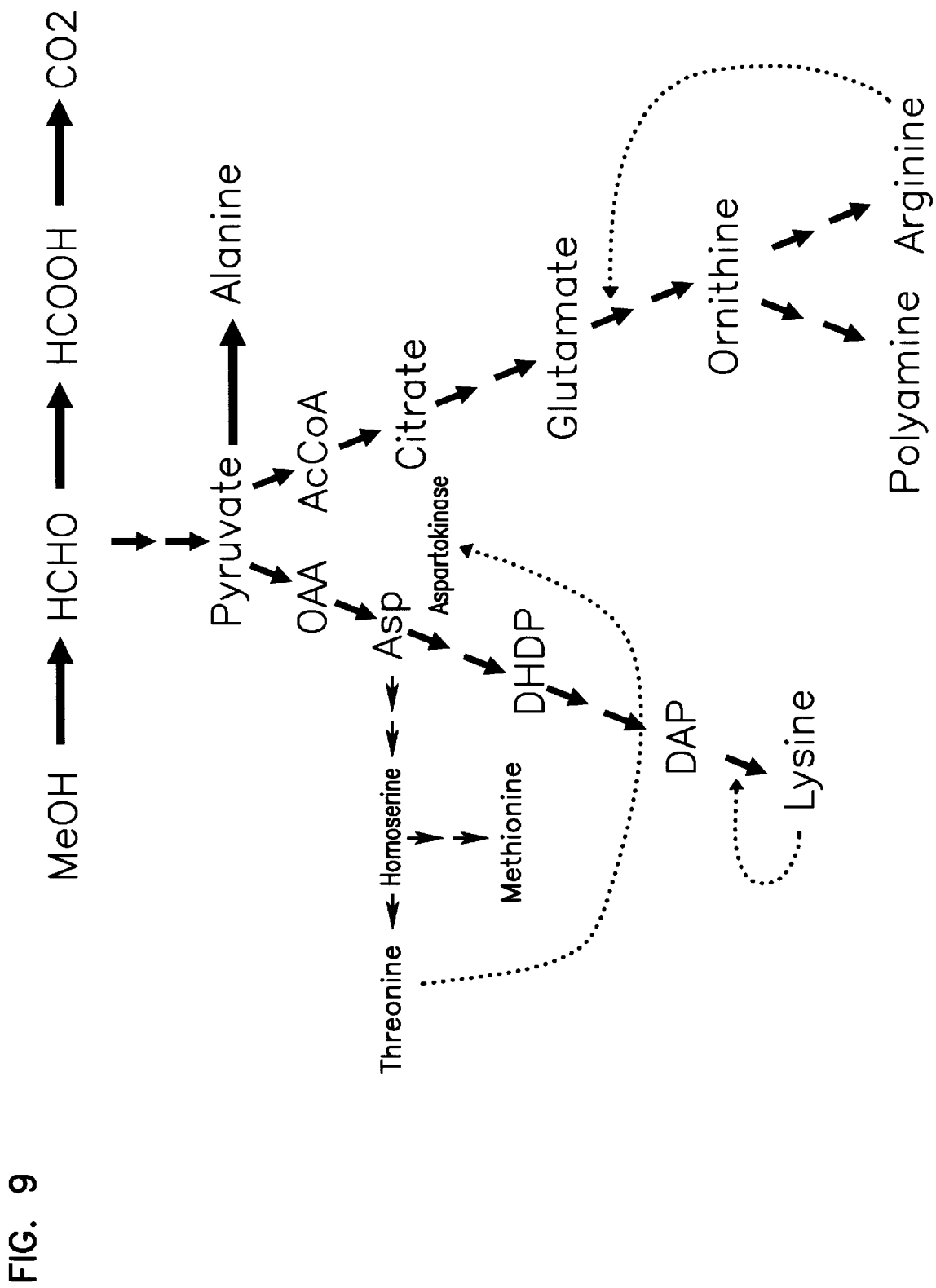
FIG. 9 shows the amino acid biosynthetic pathways employed by strains of B. methanolicus.

Primary characteristics of a Bacillus methanolicus strain of the present invention are that it is a gram positive, non-motile, spore-forming rod that can grow at 50° C. in an aqueous nutrient media that includes methanol as a sole carbon and energy source with biotin, and vitamin $B_{12}$ as required vitamins. The strains of Bacillus methanolicus are preferably isolated from environmental sources such as fresh water marsh soil or bog muck. The bacteria of the present invention are also characterized by utilization of an oxidative pathway that provides for conversion of methanol to $CO_2$ as shown in FIG. 9. This pathway also provides precursor compounds that can serve as building blocks for cellular components such as amino acids via the ribulose monophosphate pathway.

Bacillus methanolicus strains of the invention are further characterized metabolically by amino acid synthetic pathways utilizing a methanol metabolite such as formaldehyde and as shown in FIG. 9. Briefly, methanol is converted to formaldehyde by an NADH linked methanol dehydrogenase that is uniquely present in this bacterium. Pyruvate, a product of the ribulose monophosphate pathway, serves as a precursor to the production of alanine, aspartic acid, lysine, glutamic acid, and arginine in three separate pathways. While not in any way meant to limit the invention, it is believed that production of lysine by Bacillus methanolicus can be stimulated in the presence of excess amounts of aspartate and conditions which minimize feedback inhibition of aspartokinase by lysine and/or threonine and diaminopimelate decarboxylase by lysine. It is also believed that production of glutamate can also be stimulated by threonine limitation.

Figure 1:
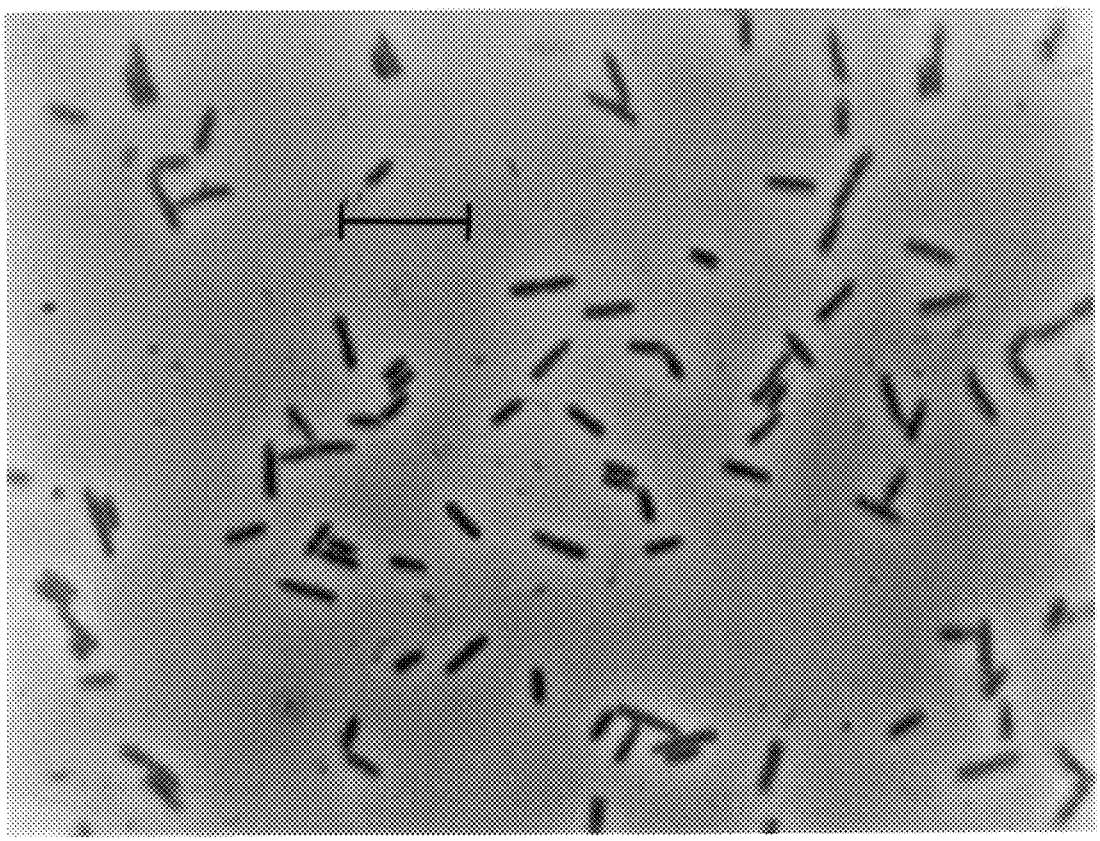
FIG. 1 is a phase contrast photomicrograph of strain MGA3 grown on MV medium at 53° C. The bar indicates 10 μm.

Specific examples of the bacteria of the invention include *B. methanolicus* strains MGA3, Gr and NOA2. *B. methanolicus* strain MGA3 isolated in the manner described herein, from fresh water marsh soil, exhibited the characteristics indicated in Table I. The cell morphology is shown in FIG. 1. *B. methanolicus* MGA3 has been deposited with the American Type Culture Collection in Rockville, Md., and given Accession No. 53907.

Figure 2:
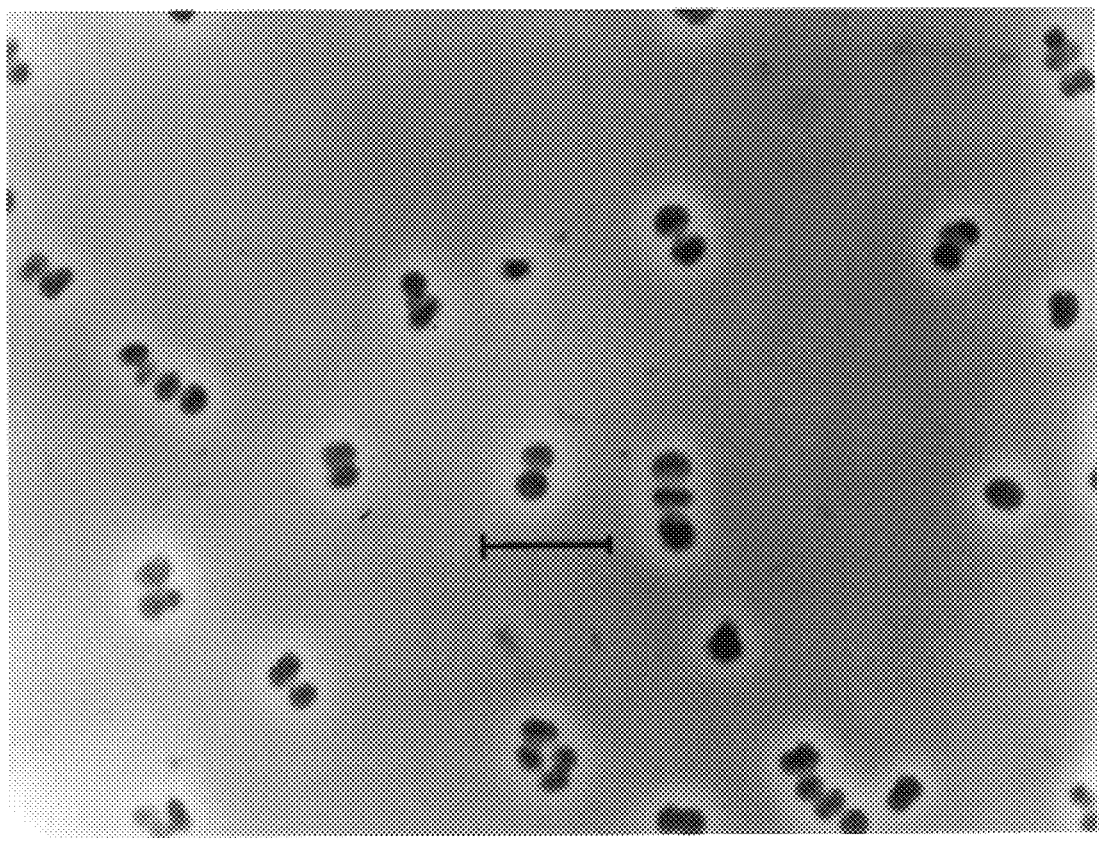
FIG. 2 is a phase contrast micrograph of strain Gr grown on MV medium at 45° C.

The bacterium is further characterized by morphological variants which can be large pleomorphic cells occasionally visible in smears of strain MGA3 cultures. These pleomorphic cells were reminiscent of the pleomorphic cells seen in an original fermentor enrichment. A colony from a plate of MGA3 produced a pure culture of a morphological variant (FIG. 2). It was designated strain Gr. This strain shared most of the cultural and physiological characteristics of strain MGA3 that were tested. Strain Gr grew on methanol or mannitol at 50° C., was neutrophilic, and required vitamin $B_{12}$ and biotin for growth, and resembled strain MGA3 in all other characteristics tested (Table I). Crude extracts of strain Gr also contained hexulose-phosphate-synthase activity. Strain Gr formed phase bright spores when a culture was switched from the non-permissive 53° C. to 37° C. A culture of strain Gr grown at high temperature did not survive heat inactivation but cells from a culture incubated an additional 18 hours at 37° C. survived 80° C. for 10 minutes. The gross appearance of Gr was similar to the rod mutants of *Bacillus subtilis* and *Bacillus licheniformis* isolated by Rogers et al., *J. Gen. Microbiol.*, 61: 155–171 (1970).

Another strain of *Bacillus methanolicus* designated strain NOA2 was isolated from pasteurized bog muck. NOA2 was isolated by the same method as *Bacillus methanolicus* strain MGA3, but grown as a batch culture at 37° C. Strain NOA2 exhibits the same species characteristics of MGA3 and as described Table I.

As described herein "aqueous nutrient media" refers to a water based composition including minerals and their salts necessary for growth of the bacterium of the present invention. Preferred nutrient media contains an effective amount of a phosphate source, a nitrogen source, a sulfate source, calcium and trace elements. As described herein "trace elements" refers to elements essential for growth in trace concentrations i.e., minute fractions of 1 percent (1000 ppm or less). As indicated in Table I, the bacterium of the present invention can utilize a number of carbon and energy sources for growth other than methanol; including glucose or mannitol; however the preferred carbon and energy source is methanol.

A satisfactory media for culturing the bacteria of the present invention is a minimal salts media, such as that described in Example 1 or the like. In a preferred embodiment, such as Example 1, minimal salts media to grow the bacterium of the present invention includes from about 20 to about 500 mm ammonium sulfate; from about 10 to 125 mM potassium phosphate, from about 0.1–1.5 mM calcium chloride; and salts of magnesium, and the trace metals: iron, copper, manganese, zinc, molybdenum, borate and cobalt in concentrations as stated in Example 4. The amount of methanol and vitamin $B_{12}$ needed for growth can vary. The amount of methanol in the media can range from about 0.05% wt/vol. to about 5% wt/vol., with amounts of from about 0.2% wt/vol. to about 0.5% wt/vol. preferred. The media should contain at least 0.05% wt/vol. methanol. The amount of vitamin $B_{12}$ in the aqueous media can range from about 0.5 $\mu g/l^{-1}$ to 1 $mg/l^{-1}$, with amounts from about 1 $\mu g/l^{-1}$ to 0.1 $mg/l^{-1}$ preferred. Optimal growth of the bacterium takes place at 45–55° C. within a pH range of about 6.0–8.0. No growth occurs when the pH is 5.5. Growth requires biotin in amounts from about 20 $\mu g/l^{-1}$ to 20 $mg/l^{-1}$. When grown in minimal salts media with methanol, vitamin $B_{12}$ and biotin the bacterium of the present invention can grow at a rate from about 0.2 $hr^{-1}$ to about 1.5 $hr^{-1}$. at a temperature of about 50° C. to 60° C.

B. Formation of Auxotrophs

A bacterium of the present invention is also characterized by its ability to form morphological mutants such as strain Gr and auxotrophs capable of producing amino acids. The bacterium also produces endospores at 37° C. and not above about 50° C. which is important to strain preservation. As defined herein "auxotroph" refers to an organism requiring specific growth factors in addition to the carbon source present in a minimal nutrient media. With respect to the present invention, auxotroph refers to mutagenized forms of *Bacillus methanolicus* strains which require one or more amino acids for growth and overproduce and excrete one or more amino acids. As defined herein "mutation" in general refers to a sudden heritable change in the phenotype of an organism which can be spontaneous or induced by known mutagenic agents, including radiation and various chemicals. Auxotrophs of the present invention can be produced using a variety of mutagenic agents including radiation such as ultra-violet light, x-rays, chemical mutagens, site-specific mutagenesis and transposon mediated mutagenesis. Examples of chemical mutagens are ethyl methane sulfonate (EMS), diepoxyoctane, N-methyl-N-nitro-N'-nitrosoguanine (NTG) and nitrous acid.

The present invention is also directed to production of amino acid analog resistant strains of *Bacillus methanolicus* that overproduce and excrete various amino acids. As defined herein "amino acid analog" refers to a compound structurally similar to an amino acid but which does not react with the biosynthetic enzymes and genetic control elements in the same way as the natural amino acid. Examples of such structurally similar analogs and their related amino acid are 5-methyl-DL-tryptophan (MT), p-fluorophenylalanine, 5-fluoro-DL-tryptophan (FT), S-2-aminoethyl-L-cysteine (AEC), methyllysine, hydroxylysine, hydroxynorvaline (threonine antagonist), and ethionine.

As described in the Examples, amino acid producing mutants of *Bacillus methanolicus* of the present invention are produced by treating the bacteria with an amount of mutagenic agent effective to produce mutants that overproduce one or more amino acid. While the type and amount of mutagenic agent to be used can vary, use of EMS and NTG in amounts from about 10 and 50 $\mu g.ml^{-1}$, respectively is preferred. After mutagenic treatment, isolates of the treated bacterium are tested for growth on media containing at least vitamin $B_{12}$ and biotin and one or more amino acids. One suitable medium to select amino acid excreting mutants is minimal vitamin media of the type described in Example 1 or the like. Auxotrophic isolates are identified by their ability to grow only on minimal vitamin media containing one or more specific amino acids. Numerous amino acid auxotrophs of the present invention were generated and are identified in Example 2.

Auxotrophs of strains of *Bacillus methanolicus* can be generated readily using UV irradiation. Briefly, an auxotroph is grown to mid exponential phase (A600=0.5–0.6) in a media containing methionine and threonine. The culture is then exposed to UV irradiation at 254 nm, preferably for a period of time less than one minute. Mutagenized cells were left to grow in the dark for 3 hours. Cells were then selected by growth in the presence of increasing amounts of s-2-aminoethyl-L-cysteine. Single colonies were isolated and plated onto plates lacking threonine and methionine to confirm auxotrophy. As shown in Example II, numerous amino acid auxotrophs were generated using mutagenesis with UV irradiation.

Other methods of mutagenesis are known to those of skill in the art, and could be readily employed to produce auxotrophs of the invention. For example, site specific mutagenesis or transposon mediated mutagenesis could be used to create homoserine auxotrophs by inactivation of genes encoding enzymes required to produce homoserine. In addition, generation of mutants of aspartokinase or diaminopimelate decarboxylase could lead to overproduction of lysine. Techniques such as transposon mediated mutagenesis and site specific mutagenesis can be conducted on strains of *Bacillus methanolicus*, as described by Bohanon et al., "Isolation of auxotrophic mutants of methylophilus methylotrophus by modified marker exchange", *Appl. Environ. Microbiol.,* 54: 271–273 (1988) and Simon et al., "A broad host range mobilization system for in vitro genetic engineering: Transposon mutagenesis in gram negative bacteria", *Bio/Technology,* 1: 784–791 (1983), which are hereby incorporated by reference.

Several auxotrophic mutants of *Bacillus methanolicus* strain NOA2 are generated by UV irradiation and can be further selected by exposure to lysine analogs s-2-aminoethyl-L-cysteine (AEC), hydroxylysine, methyllysine and mixtures thereof. These auxotrophs are homoserine auxotrophs and require both methionine and threonine for growth. The auxotrophs also overproduce and excrete at least one amino acid. The preferred auxotrophs of the invention are those that overproduce and excrete glutamate. The auxotrophs overproduce and excrete glutamate preferably from at least about 5 gm/l to 150 gm/l, and more preferably from 50 gm/l to 150 g/l. The auxotrophs that overproduce glutamate can also coproduce one or more other amino acids such as lysine, aspartic acid, alanine, and mixtures thereof.

Auxotrophs of *Bacillus methanolicus* can also be treated alternatively or additionally with an amino acid analog to select for mutants which overproduce specific amino acids. In one preferred embodiment, amino acid producing mutants are first treated with the chemical mutagenic agent EMS (10 $\mu g.ml^{-1}$ or NTG (50 $\mu g.ml^{-1}$) or UV irradiation to produce amino acid auxotrophs. Amino acid auxotrophs are then treated with increasing amounts of the amino acid analog AEC to further select mutants.

Optionally, these mutants can be exposed to other lysine analogs such as hydroxylysine and methyllysine, and mixtures thereof or other amino acid analogs such as HNV (threonine analog). This selection process can involve a single exposure to an amino acid analog or mixtures of amino acid analogs or multiple selection steps. Preferably, between selection steps, rapidly growing isolates are assayed for amino acid production. Isolates producing the greatest amount of the desired amino acid can be further selected with the same or different amino acid analogs. In addition, the isolates can optionally be grown in the presence of increasing amounts of the desired amino acid and then grown in media without the desired amino acid and assayed for production of the desired amino acids. Isolates that can rapidly grow in the presence of the desired amino acid while still retaining the capacity to excrete the amino acid are preferred. While not in any way meant to limit the invention, it is believed that isolates that can rapidly grow in the presence of the desired amino acid and still overproduce the desired amino acid may no longer exhibit feedback inhibition of amino acid biosynthetic enzymes with the end product of the pathway. It is envisioned that the present invention can be employed to produce amino acid auxotrophs and/or amino acid analog resistant mutants of *Bacillus methanolicus* that are capable of producing most, if not all, of the known amino acids.

Several auxotrophic mutants of *Bacillus methanolicus* generated by chemical mutagenesis or UV irradiation have been deposited with the American Type Culture Collection in Rockville, Md. A homoserine auxotroph of strain NOA2 isolated after chemical mutagenesis was designated NOA2 8/16-5 and given Accession No. 55158. A homoserine auxotroph of strain Gr designated 7/30-15 was deposited with the ATCC and given Accession No. 55159. A homoserine auxotroph generated by UV irradiation of NOA2 auxotroph 8/16-5 and that excretes glutamate was designated NA#29 and deposited with the American Type Culture Collection on Mar. 17, 1993 at the American Type Culture Collection, Rockville. Md. 20852 and given Accession No. 55403.

C. Method of Producing Amino Acids: Glutamate Production

To produce amino acids from auxotrophic and/or amino acid resistant mutants of *Bacillus methanolicus*, the organism is cultured in an aqueous nutrient medium having biotin, vitamin $B_{12}$, and methanol together with amounts of a phosphate source, a sulfate source, a nitrogen source, calcium and trace elements in amounts such as indicated in Example 4. As previously described a satisfactory media is a minimal salts media, such as described in Example 1 or the like. The amounts of methanol and vitamin $B_{12}$ needed for production of amino acids can vary. Methanol can range from about 0.05% wt/vol. to 5% wt/vol. with an amount of from about 0.3% to about 0.8% wt/vol. methanol preferred. Vitamin $B_{12}$ can range from about 0.5 $\mu g/l^{-1}$ to 1 $mg/l^{-1}$. With amounts of about 1 $\mu g/l^{-1}$ to about 0.1 $mg/l^{-1}$ preferred. At a minimum, at least about 0.05% wt/vol. methanol, 0.5 $\mu g/l^{-1}$ vitamin $B_{12}$ and about 20 $\mu g l^{-1}$ to about 20 $mg/l^{-1}$ biotin are needed for mutant production of amino acids.

In a preferred embodiment, phosphate, magnesium, and calcium are fed to the media coupled to pH control with ammonium hydroxide or gaseous ammonia. Control of the pH provides for optimal growth of the auxotrophic strains of the present invention as well as enhancing glutamate production. The pH of culture can be monitored and controlled by standard methods known to those of skill in the art. Preferably the culture is maintained at a pH of about 5.5 to 7.2, and more preferably at a pH of about 6.3 to 7.2.

Many nitrogen sources can be used in the aqueous nutrient media, such as ammonium chloride, ammonium sulfate and ammonium nitrate. The preferred nitrogen sources are ammonia, ammonium chloride, or $(NH_4)_2SO_4$ required in amounts of at least 20 mmoles.

Employing auxotrophs and/or amino acid resistant mutants of *Bacillus methanolicus*, it is believed that glutamate and other amino acids can be produced in substantial quantities. That is, quantities of amino acids from at least 5 $g/l^{-1}$ to about 50 $g/l^{-1}$, and preferably from about 50 $g/l^{-1}$ to about 150 grams. The present invention is believed useful to produce glutamate either singly or in combination with many of the 19 amino acids, including lysine, aspartic acid, and/or alanine. In one embodiment, auxotrophs can produce from about 5 to about 15 $g/l^{-1}$ of glutamate. In one preferred embodiment, coproduction of at least about $5g/l^{-1}$ of L-lysine and 5 $g/^{-1}$ of L-glutamate are obtained.

When cultivated on minimal salts media of the type described in Example I, *Bacillus methanolicus* strains of the present invention can grow at cell densities up to 50 g/l$^{-1}$ dry wt. Preferably, cell growth on minimal salts media with vitamin B$_{12}$, biotin and methanol at temperatures between 45° C. and 55° C. can be at least 15 g/l$^{-1}$ (dry weight) and up to 0.6 grams of cells per gram methanol. Cell densities of 30–50 g/l$^{-1}$ (dry weight) with cell yields of about 0.53 grams cells per gram methanol have been observed.

Auxotrophs of the present invention can produce amino acids when grown in batch culture. However, fed-batch or semi-continuous feed of methanol and trace elements with required amino acids enhances amino acid production. Amino acid production by auxotrophs of the present invention can be further enhanced by using continuous culture methods in which trace elements are automatically fed with required amino acids. Further, phosphate, magnesium and calcium feeding to a batch-fed or continuous culture can be coupled to pH control. The pH is preferably maintained at a pH of about 5.5 to 7.2, more preferably about 6.3 to 7.2. Production of glutamate by auxotrophs is maximized when the bacterium of the present invention is grown to the highest cell densities by using continuous addition of methanol, and trace elements to culture media together controlling pH, with continuous addition of pure oxygen and limiting threonine.

In a preferred version, a homoserine auxotroph such as NA#29 is grown in a 14 liter fed batch fermentor in MV media. The bioreactor is operated so that the concentrations of threonine, methionine and phosphate are growth limiting when the cell density reaches 6–10 g/l of cell dry weight. Methanol is fed continually to maintain a dissolved methanol concentration of about 100 mM. The pH of the culture is maintained at about 6.3–7.1, and dissolved oxygen at 15% air saturation. The strain of bacteria is grown for 60–70 hours. Glutamate is overproduced and excreted into the media at a concentration of at least about 5 g/l. Other amino acids such as lysine or alanine can be coproduced under these operating conditions.

Fed-batch or semi-continuous culture conditions can be additionally manipulated to favor overproduction of certain amino acids over others. For example, controlled feeding of threonine during growth of the homoserine auxotrophs of the invention can lead to overproduction of glutamate. Threonine is an esssynthe amino acid that is not synthesized by homoserine auxotrophs and also can act as a feedback inhibitor of other biosynthetic enzymes such as aspartokinase III. Threonine can be fed to cultures of homoserine auxotrophs at a rate that limits the growth of the culture to slow rate but allows the culture to preferably reach about 10 to 30 grams of dry cell weight (DCW). A growth limiting amount of threonine per gram dry cell weight of a particular auxotroph can be determined by standard methods including growing the auxotroph in the presence of increasing amounts of threonine and determining the optical density of the cultures at the same time. In a typical 14 liter batch fermentor, threonine is fed at about 0.01 to 1.0 g/l/hr, preferably about 0.04–0.3 gm/l/hr (2–15 mg/g DWC/hr).

Controlled feeding of threonine can include adding threonine at constant growth limiting rate or by changing the amount of threonine from nonlimiting to limiting concentration in a stepwise manner. For example, when the threonine concentration supplied to a culture is changed in a stepwise manner, threonine is initially added at a higher non-limiting concentration to provide for cell growth of the auxotroph to a sufficient cell density. Once the culture reaches that density, the threonine concentration is decreased at least about 5-fold or eliminated. Under this type of stepwise controlled feeding of threonine, glutamate can be produced at about 5 g/l simultaneously with or after lysine has begun to accumulate. Controlled feeding of threonine at a constant growth limiting rate can also favor coproduction of lysine up to 28 gm/l and glutamate can be produced at 10–15 g/l.

Amino acid production of an auxotroph of *Bacillus methanolicus* can be controlled by threonine feeding to enhance overproduction of a single amino acid, such as glutamate, or two or more amino acids, such as glutamate and lysine. The overproduction of a single amino acid such as glutamate is favored when a step change is made in threonine feeding, i.e., threonine is initially fed at nonlimiting concentrations and then decreased about 5-fold or more. The overproduction of two or more amino acids, such as lysine and glutamate, can occur when threonine is fed at a constant growth-limiting rate.

While not in any way meant to limit the invention, it is believed that deregulation of certain key enzymes in the biosynthetic pathways shown in FIG. 9, provides for overproduction of amino acids, such as lysine or glutamate. For example, it is believed that lysine production in strains of *Bacillus methanolicus* is regulated by feedback inhibition of aspartokinase and/or diaminopimilate decarboxylase. Since aspartokinase is feedback inhibited by threonine, lysine production could be increased by decreasing feedback inhibition of aspartokinase by limiting the amount of threonine present.

If desired, the amino acid produced in the culture can be separated using known extraction procedures such as ion exchange chromatography. In a preferred method the fermentation broth including the *Bacillus methanolicus* strain, culture media components and amino acids produced is dried directly to produce a material containing cells, media components and one or more over produced essential amino acids which are useful as an animal feed or animal feed supplement. The fermentation broth can be dried by, for example, the method reported in G. L. Solomons, *Materials and Methods in Fermentation*, (Academic Press, N.Y. 1964).

EXAMPLE 1

Isolation and Characterization of *Bacillus methanolicus* Strain MGA3

A. METHODS AND PROCEDURES

Growth and Sporulation Media

Minimal salts medium (MS) contained in one liter of distilled water: K$_2$HPO$_4$, 3.8 g; NaH$_2$PO$_4$.H$_2$O, 2.8 g; (NH$_4$)$_2$SO$_4$, 3.6 g; MgSO$_4$.7H$_2$O, 0.5 g; FeSO$_4$.7H$_2$O, 2 mg; CuSO$_4$.5H$_2$O, 40 µg; H$_3$BO$_3$; 30 µg; MnSO$_4$.4H$_2$O, 200 µg; ZnSO$_4$.7H$_2$O, 200 µg; Na$_2$MoO$_4$, 40 µg; CaCl$_2$.2H$_2$O, 5.3 µg; CoCl$_2$.6H$_2$O, 40 µg. The pH of this medium was adjusted to 7.0 prior to autoclaving. The phosphates were reduced by 50% when MS medium was used for continuous cultures.

The minimal vitamin medium (MV) was MS medium supplemented with thiamine.HC1, D-calcium pantothenate, riboflavin, and nicotinamide, each at 50 µg/l$^{-1}$, biotin and folic acid, each at 20 µg/l$^{-1}$ and B$_{12}$ at 1 µg/l$^{-1}$.

Yeast extract medium (MY) was MS medium supplemented with yeast extract 0.5 g/l$^{-1}$.

All media (MV and MY) contained 0.4% (vol/vol) methanol unless otherwise stated. Nutrient broth (NB) contained beef extract 3 g and peptone 5 g in 1000 ml distilled water. J vitamin medium (JV) contained tryptone (5 g) and yeast extract (15 g) per liter and the vitamins at the same concentration as MV medium. Sporulation medium (SM) was composed of three parts NB and four parts MV medium. All solid media was prepared by combining double strength medium components with an equal amount of 3% bacto agar after autoclaving.

Enrichment

Freshwater marsh soil was suspended in distilled water and heated for 20 minutes at 90° C. A portion of this suspension was used as an inoculum for the fermentors operating as batch cultures at 53° C. When growth was apparent in the vessels, the medium pumps were turned on and the flow rate was gradually increased to produce continuous cultures for enrichment.

Continuous Cultures

Two 1-liter Omni-Culture fermentors (The Virtis Company, Gardiner, N.Y.) were used for continuous cultures. A metering pump (Ismatec Mini, Chicago, Ill., S-820) fed an unsterilized MS medium into the vessels and flow was adjusted between 0.1 and 0.5 volumes per hour. A separate metering pump fed methanol at a rate that maintained a residual concentration of approximately 2 $g/l^{-1}$ in the outflow. The concentration of methanol was measured by gas chromatography. The pH was automatically controlled at pH 6.8 by the addition of 10% v/v ammonium hydroxide (Controller Model 5656-00, Cole Parmer Instrument Co., Chicago, Ill.). The temperature was maintained between 53° C. and 56° C. Air was sparged at 2 v/v/m and three flat blade turbine impellers were operated at 600 RPM.

Isolation of Pure Cultures

Samples from the fermentors were periodically streaked on MY and MV agar and incubated at 53° C. Isolated colonies that were obtained from these plates were restreaked and grown under the same conditions. Colonies were tested for growth on methanol by inoculating 2 ml of MV medium into 18 mm tubes and incubating the tubes in a gyratory water bath shaker at 53° C. Tubes with growth in this methanol minimal broth were streaked onto MV agar for further purification.

Morphological Characteristics

Gram strain, spore strain, and poly-β-hydroxy-butyrate straining were done as described in the Doetsch, *Manual of Methods for General Bacteriology* at pp. 21–33 (American Society for Microbiology, 1981). Gram strains were verified with the KOH test conducted as described by Gergersen, supra. Cell size was determined with cells grown on MY agar for 18 hours at 50° C.

Characterization Tests

The API Rapid CH and Rapid E strip systems (Sherwood Medical, Plainview, N.Y.) were used to provide a standardized fermentation study of 49 substances and nine additional biochemical determinations respectively. Cultures used to inoculate two sets of strips were grown for 18 hours at 55° C. on the JV agar medium and on SM agar medium. The test strips were inoculated and read according to the directions provided with the system. Tests for nitrate reduction, NaCl tolerance, tyrosine decomposition, and lysozyme tolerance were performed as described by Gordon et al., *The Genus Bacillus Handbook No. 427* (Washington, D.C., Dept. of Ag. (1973)), but with the following changes. The reduction of nitrate to nitrite, NaCl tolerance, and lysozyme tolerance were tested in JV medium; tyrosine decomposition was tested in JV medium with tyrosine (5 $g/l^{-1}$) and 0.5% methanol. To test the suitability of nitrate as an nitrogen source, potassium nitrate (5 $g/l^{-1}$) was substituted for the ammonium sulfate in the MV medium.

Hydrolytic Activity

MV agar plates with 0.5% (vol/vol) methanol, were prepared to detect hydrolytic activity by adding soluble starch (3 $g/l^{-1}$), fruit pectin (Certo Brand, 10 $g/l^{-1}$), and gelatin (Sigma Type I, 4 $g/l^{-1}$) to MV media prior to pouring the plates. Plates containing casein were prepared with 15 g non-fat dry milk (Carnation Company) in a liter of half-strength MV media. Hydrolysis on these plates was detected as described in Laskin and Lechevalier, *CRC Handbook of Microbiology*, pp. 734–735 (CRC Press, 1971).

Dipicolinic Acid Extraction and Determination

Dipicolinic acid (DPA) was extracted by autoclaving 5 ml samples of cell suspensions for 20 minutes. The samples were then cooled, acidified with 1 ml of 1N acetic acid, allowed to stand for 1 hour, and then centrifuged at 12,000×g for 10 minutes. The amounts of DPA in the supernatant fractions were determined by the calorimetric assay described by Janssen et al. *Science*, 127: 26–27 (1958). Sporangia and cell counts were determined visually with the use of a Petroff-Hauser counting chamber.

Heat and chloroform resistance

A portion of culture was heated to 80° C. and then maintained at 80° C. for 10 minutes. Viable and heat stable counts were determined by plating appropriate dilutions of the heated and unheated culture on MY agar. The plates were incubated at 45° C. for 48 hours before the colonies were counted. A spore suspension was prepared from a culture grown at 50° C. for 18 hours and at 37° C. for 18 hours in MY. The culture was centrifuged at 12,000 g, washed, in distilled water by centrifugation and resuspended in distilled water. The spore suspension was pasteurized at 65° C. for 10 minutes. A portion of this suspension was then heated at 80° C. for 10 minutes. Spore counts were determined by plating dilutions on MV agar and incubating the plates at 50° C. for 48 hours.

Chloroform, 5 μl, was added to test tubes (13 mm×100 mm) containing 1 ml of a culture. After mixing the suspension on a vortex mixer, the tube was incubated at 37° C. for 10 minutes prior to dilution and plating as described above.

Growth Experiments

The growth responses to various substrates were determined in MV medium containing alcohols, at 0.5% (vol/vol); sugars, organic acids and methyl substituted amines, each at 0.3% (wt/vol); and formaldehyde, at 0.03% (wt/vol). The effects of pH on growth were determined in MV medium with the pH adjusted by addition of HCl or NaOH. Growth rates were determined by growth of culture in triple baffled flasks (Bellco Model 2540) on a gyratory shaker (New Brunswick Model G-7) operated at approximately 200 RPM. Growth was measured by turbidimetric measurements at 650 nm using a spectrophotometer or Klett units (#66 filter), using a Klett Summerson calorimeter. One absorbance unit was equivalent to 0.42 $g/l^{-1}$ of dry cell weight.

Antibiotic Susceptibility

An 0.2 ml volume of a mid-exponential phase culture was spread onto MV agar plates containing 0.5% vol/vol methanol. The plates were incubated for 1 hour at 55° C. to dry the surface. Antibiotic containing discs (Difco Laboratories, Detroit, Mich.) were then aseptically placed on the surface and the plates were returned to 55° C. for 48 hours. The antibiotic discs used to test susceptibility contained gentamicin 10 mcg, sulfadiazine 300 mcg, tetracycline 30 mcg, ampicillin 10 mcg, rifampin 5 mcg, chloromycetin 30 mcg, erythromycin 5 mcg, and penicillin G 10 units.

Methanol Oxidation

Cultures of Bacillus strain MGA3 were grown to mid-exponential phase in liquid MV media with methanol (4 $g/l^{-1}$) or mannitol (3 $g/l^{-1}$) at 50° C. Cells were harvested at 4° C. by centrifugation at 12,000×g for 8 minutes, washed by centrifugation in ice cold 0.05M phosphate buffer pH 7.0 and suspended in ice cold 0.05M phosphate buffer. Methanol oxidation was measured using a Rauk oxygen electrode (Rauk Bros., Bottisham, England). Oxygen consumption was measured by placing a suspension of cells (3.7–7.3 mg/ml$^{-1}$) in 0.05M phosphate buffer in the electrode. After the rate of endogenous oxygen consumption was established, methanol 1.0 g/l$^{-1}$ was added to the electrode and the rate of methanol dependent oxygen consumption was measured.

Crude Extracts and Enzyme Assays

Cells were harvested in mid-exponential phase, resuspended in 50 mM phosphate buffer, pH and disrupted by two passages through a French pressure cell operated at 15,000 psi. The cell debris was separated by centrifugation at 12,100 g and the supernatant fraction was used as the crude extract. Hexulose phosphate synthase was assayed by the method of Cox and Zatmann, *J. Biochem,* 141: 605–608 (1974), incorporated by reference herein; and hydroxypyruvate reductase was assayed by the method of Large and Quayle, *J. Biochem,* 87: 387 (1963), incorporated by reference herein. Protein concentrations were determined with Biuret reagent by the method of Clark and Switzer, *Experimental Biochemistry* (2nd ed., Freeman Press, 1977), incorporated by reference herein. Bovine serum albumin was employed as a standard.

DNA Base Composition

The DNA base composition was determined by measuring the hyperchromic shift in absorbance as a function of temperature in 0.12M sodium phosphate pH 6.8 with *E. coli* DNA as a standard, Mandel and Marmur, *Methods Enzymol.,* 12: 195–206 (1968).

B. RESULTS

Enrichment and Isolation

Development of a methanol-utilizing mixed culture at 53–56° C. was rapid and abundant. When a continuous culture was established, dilution rates could be raised to 0.45 per hour without washout. Smears revealed a preponderance of Gram positive forms including spore-forming bacteria, and a variety of morphological types including some very large pleomorphic cells. However, only bacteria that did not grow when returned to methanol minimal medium could be readily isolated from the enrichment vessels. After screening many isolates, (using the isolation procedure described above one was found that grew rapidly in MV medium at 53° C. and was given the strain designation MGA3.

Cell and Colony Morphology

Cells of strain MGA3 were rod shaped (0.8–1.0 by 2.5–4.5 μm) with rounded ends (FIG. 1). Young cultures stained Gram positive and all cultures were KOH negative. V-shaped pairs of cells were frequent in cultures. Vacuoles were never seen and poly-β-hydroxybutyrate was not detected by Sudan black B staining. Colonies produced on MV agar were colorless, translucent, circular, convex, and had entire margins. Streak cultivation produced colonies of various sizes and all colonies grew larger on MV agar supplemented with amino acids, glucose, yeast extract, or small amounts of nutrient broth than on unsupplemented MV agar. Pigments were not produced.

Endospores

Figure 3:
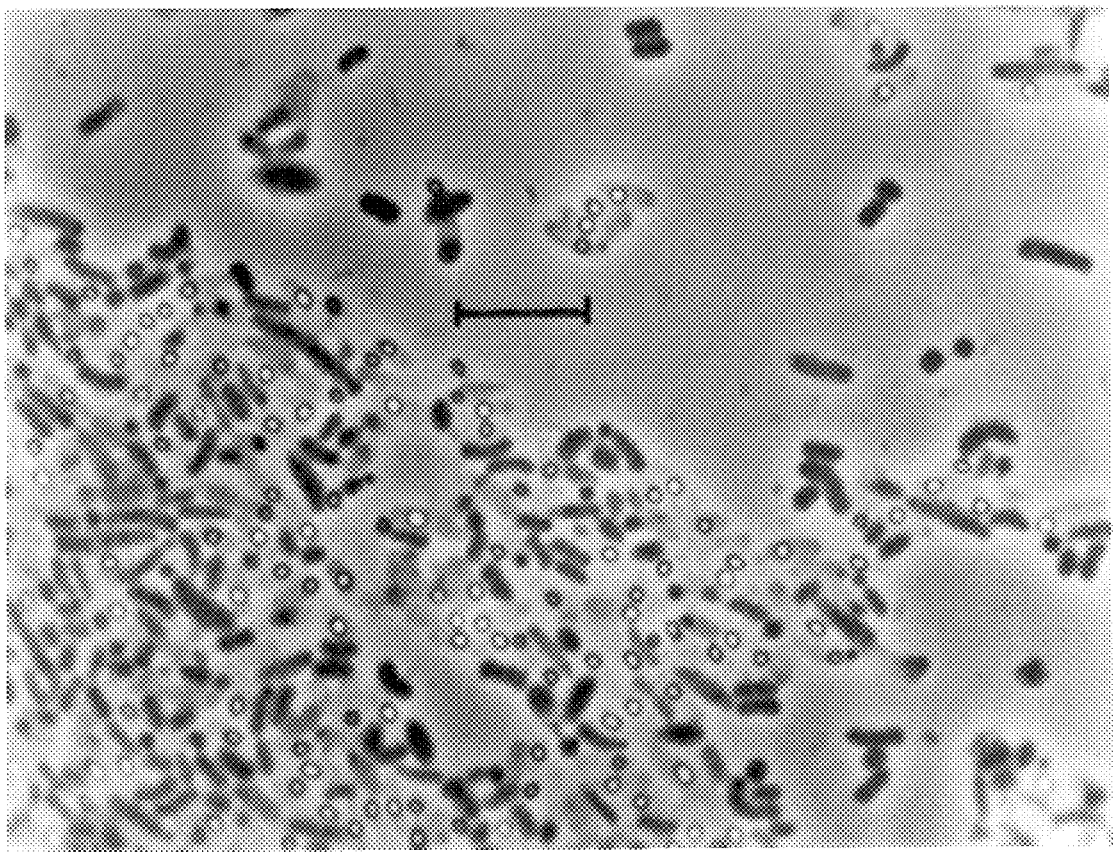
FIG. 3 is a phase contrast photomicrograph of strain MGA3 grown on SM medium at 53° C. and shifted to 37° C. The bar represents 10 μm.

Spores were oval and 0.8–1.0 by 1.1–1.2 μm, their location was subterminal and sporangia were swollen (FIG. 3). It was noticed that most cultures grown on MV agar at 53° C. did not contain refractile endospores and lost viability rapidly when stored at room temperature. These cultures did not grow when inoculated into fresh media. However, cultures that contained endospores produced growth in fresh media even after heating at 80° C. for 10 minutes. Strain MGA3 grew well at 50–55° C. but most cells lysed without producing endospores. It was noted that endospores were formed in cultures that were incubated at 50–55° C. for 18 hours and then incubated at 37° C. for an additional 18 hours. When cultures were grown under these conditions 54% of the cells contained refractile endospores and chloroform resistant colony forming units were equal to 10% of the viable cell counts ($2.7 \times 10^{-7}$ viable cells.ml$^{-1}$). It was also noted that supplemented methanol media (MY,SM) produced more endospores than the minimal medium (MV). Nutrient agar or nutrient agar with added manganese sulfate (5 mg.l$^{-1}$) did not serve as a good sporulation media.

Heat Tolerance

Exponential-phase cultures of MGA3 grown at 50° C. and containing $3.1 \times 10^8$ colony forming units (CFU) per ml were completely killed by heating for 10 minutes at 80° C. A pasteurized spore suspension from cultures grown 18 hours at 53° C. and incubated an additional 18 hours at 37° C. contained $7.37 \times 10^7$ CFU when plated on a methanol-salts medium (MV). The same suspension contained $3.5 \times 10^7$ CFU after heating at 80° C. for 10 minutes.

Dipicolinic Acid

Dipicolinic acid is a compound absent from vegetative bacteria but present in large amounts in endospores. A culture of *Methylophilus methylotrophus* grown in MV medium at 37° C. and a culture of strain MGA3 grown in MV at 50° C. and then switched to 37° C. were each the source of 70 mg (wet weight) of cell paste. Each cell paste was extracted and assayed for dipicolinic acid. The cells of *Methylophilus methylotrophus* contained no detectable dipicolinic acid while the cells of MGA3 contained 0.189 mg dipicolinic acid.

Growth

Strain MGA3 grew well in J medium, a complex medium used to grow fastidious species of Bacillus, Gregersen, *Eur. J. Appl. Microbiol. Biotechnol.,* 5: 123–123 (1978) incorporated by reference herein, and grew poorly in nutrient broth or on nutrient agar. The organism grew rapidly in MV medium that contained methanol or mannitol. Of the vitamins present in this medium, only vitamin $B_{12}$ stimulated growth and both vitamins $B_{12}$ and biotin was absolutely required for growth. Strain MGA3 grew more slowly when the medium contained glucose as the source of carbon and energy. Maltose, ribose, acetate, glutamate, and alpha-ketoglutarate were utilized poorly, and growth from galactose was scant or doubtful. Lactose, sucrose, xylose, formate, succinate, glycerol, ethanol, n-propanol, n-butanol, formaldehyde, methylamine, diethylamine, or trimethylamine were not utilized.

Acid was produced from only 7 of the 49 substrates used in the API rapid CH test (ribose, D-glucose, mannitol, maltose, D-tagatose, D-arabitol, and 5-keto-gluconate). Gas was not produced from any of the following substrates:

Glycerol, erythritol, D-arabinose, L-arabinose, D-xylose, L-xylose, adonitol, beta-methyl-xyloside, galactose, D-fructose, D-mannose, L-sorbose, rhamnose, dulcitol, inositol, sorbitol, alpha-methyl-D-mannoside, alpha-methyl-D-gluconate, N-acetyl-glucosamine, amygdalin, arbutin, esculin, salicin, cellobiose, lactose, melibiose, saccharose, trehalose, insulin, melezitose, D-raffinose, starch, glycogen, xylitol, β-gentiobiose, D-turanose, D-lyxose, D-fucose, L-fucose, L-arabitol, gluconate, or 2-keto-gluconate.

Strain MGA3 grew in JV broth that contained 1% NaCl but not in broth that contained 5% NaCl.

Growth on Methanol

Of the eight vitamin components in MV medium, only vitamins $B_{12}$ and biotin was required for growth of strain MGA3 on methanol. If vitamin $B_{12}$ is eliminated from MV medium, growth of strain MGA3 does not occur. Nitrate was not utilized as a nitrogen source.

Growth of strain MGA3 in methanol was optimal at pH 7.0–7.5. Growth did not occur at pH 5.5. The optimum growth temperature was found to be between 50° and 53° C. The organism grew in MY medium at 30 and at 61° C.; it failed to grow at 25 and 65° C.

TABLE II

The effect of temperature on the growth rate of Bacillus Strain MGA3 in medium MV.

| Temperature Degree | $\mu(h^{-1})$ |
|---|---|
| 37 | 0.24 |
| 45 | 0.41 |
| 50 | 0.51 |
| 53 | 0.43 |
| 56 | 0.38 |

Figure 4:
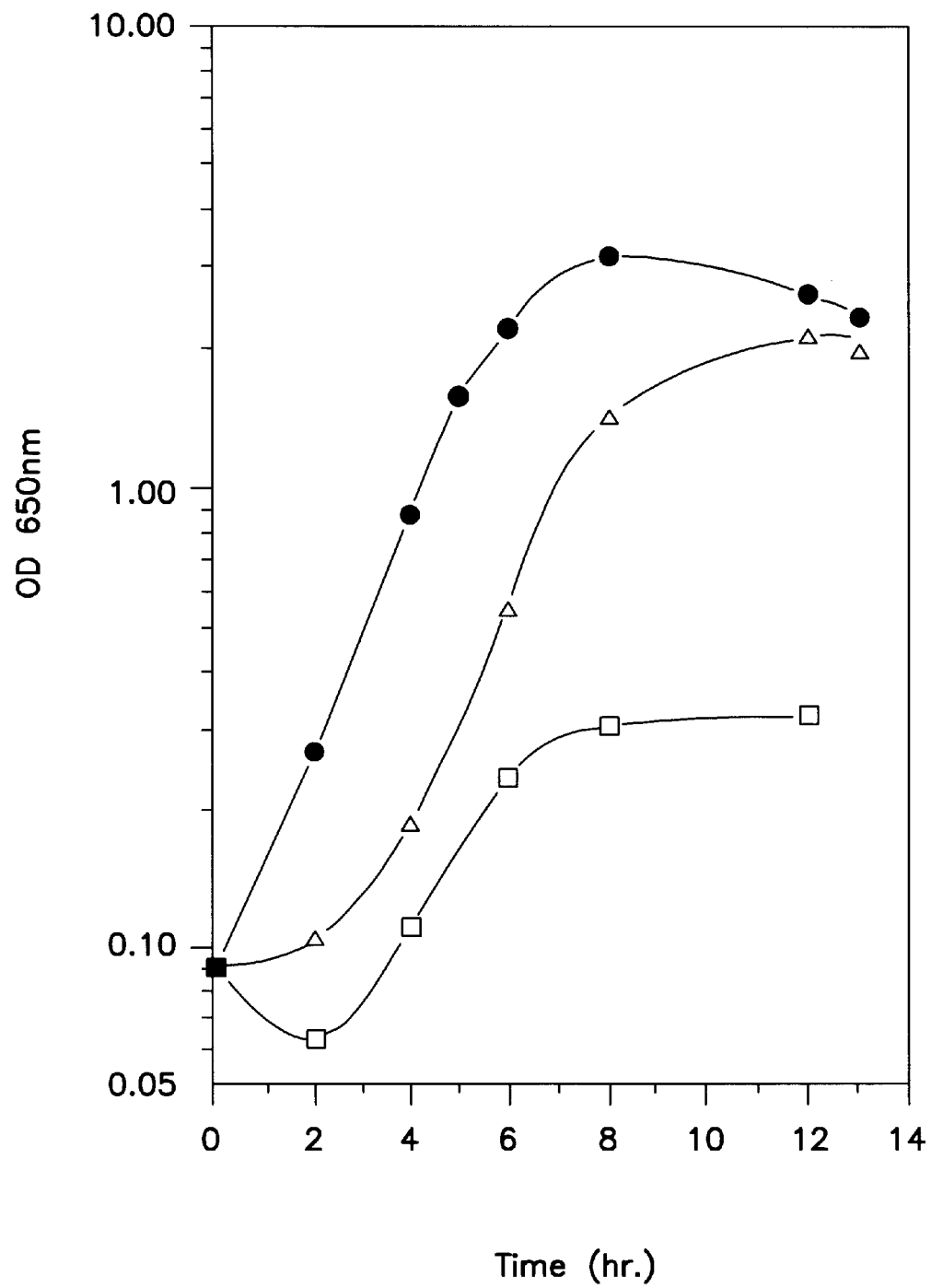
FIG. 4 shows growth of Bacillus methanolicus strain MGA3. Strain MGA3 was inoculated into MV media containing 0.5 g/l$^{-1}$ yeast extract (-⋈-), methanol 5.0 g/l$^{-1}$ (-Δ-), or methanol 5 g/l$^{-1}$ and 0.5 g/l$^{-1}$ yeast extract (-●-). The cultures were incubated with shaking at 53° C.

Strain MGA3 had a generation time of 1.4 hours in MV medium at 50° C. Growth on methanol was stimulated by the small additions of complex nutrient mixtures such as yeast extract. Generation times were reduced to approximately 1 hour in these media (FIG. 4).

Biochemical Characterization

Crude cell extracts prepared from methanol grown cultures of MGA3 lacked hydroxypyruvate reductase activity but contained high hexulose-6-phosphate synthase activity. The specific activity of hexulose-6-phosphate synthase was 6.27–3.72 $\mu$m of formaldehyde utilized per minute per mg of protein. Strain MGA3 did not produce catalase or tyrosine-degrading enzymes. Starch, gelatin, and pectin were hydrolyzed but growth was inhibited on casein containing plates. The API Rapid E tests indicated the presence of cytochrome oxidase, urease and acetoin. The Rapid E tests for $\beta$-galactosidase, lysine decarboxylase, ornithine decarboxylase, citrate utilization, phenylalanine deamination, and indole were negative. Nitrate was not reduced to nitrite.

Methanol oxidation by cell suspensions grown with methanol or mannitol as carbon and energy sources was measured at 50° C. and 37° C. Cells grown with methanol as the carbon and energy source oxidized methanol at a rate of $5.8 \times 10^{-4}$ mMoles.min$^{-1}$.mg$^{-1}$ at 37° C. Cells grown with mannitol as the carbon and energy source oxidized methanol at a rate of $6.5 \times 10^{-5}$ mMoles.min.mg$^{-1}$ at 50° C.

Antibiotic Susceptibility

Strain MGA3 was sensitive to all antibiotics tested.

DNA Base Composition

DNA isolated from strain MGA3 had a base content of 44 moles per cent G+C.

A comparison of the identifying characteristics of Bacillus strain MGA3 with those described for strains of *Bacillus methanolicus* in Arfman et al., cited supra., indicates that Bacillus MGA3 can be classified as a strain of *Bacillus methanolicus*.

EXAMPLE 2
A. PRODUCTION OF AUXOTROPHIC MUTANTS

Amino acid auxotrophs and glutamate and lysine producing strains were derived from two environmental isolates, *Bacillus methanolicus* strains MGA3 and NOA2. Bacillus MGA3 was isolated from a continuous culture as described in Example 1 above. NOA2 was isolated by the same method but from a 37° C. batch culture employing MV medium, 2% (vol/vol) methanol, and inoculated with pasteurized bog muck. NOA2 exhibits the same species related characteristics of MGA3 as described in Example 1.

The standard mutagenesis, used to derive both amino acid auxotrophs and analog resistant mutants, was a treatment with ethyl methane sulfonate (EMS) or N-methyl-N-nitro-N'-nitrosoguanine (NTG). The cells to be mutagenized were grown to late log phase (2.5 OD) in MV medium plus casamino acids (CAA 0.2%). The culture (2.5 ml) was combined with an equal amount of fresh medium and the chemical mutagen was added in the following amounts:

|  | per ml | minutes | ° C. |
|---|---|---|---|
| NTG | 50 $\mu$g | 10–15 | 50 |
| EMS | 10–20 $\mu$l | 20–25 | 37 |

This was followed by dilution and outgrowth in a medium containing either casamino acids (0.2–0.4%), the amino acids of interest (50 mg/l), or both. After 6 hours outgrowth, this culture was diluted with three parts carbon free medium and incubated at 37° C. for 18 hours. Spores were centrifuged, washed twice, and the spore suspensions were stored at 4° C. Appropriate dilutions of spore suspensions were plated on amino acid containing agar and incubated at 50° C. for 36 hours. Colonies were replicated to amino acid containing media and minimal media, and incubated overnight at 50° C. Colonies that appeared to require one or more amino acids for growth were tested for growth on individual amino acids and mixtures of amino acids in order to define the specific amino acid requirements. The mutagenic treatments that produced mutants important to the production lysine, glutamate, tryptophan, phenylalanine and other amino acids are outlined in the following Table:

TABLE IV

Production of Auxotrophs

| Parent | Date | Agent | Conditions Conc.[1]min. | | New Mutant |
|---|---|---|---|---|---|
| Gr | 07/22/88 | NTG | 50 | 10 | 7/30–15(hse$^-$) (ATCC No. 55159) |
| MGA3 | 12/08/87 | EMS | 10 | 15 | S12 (hse$^-$) (ATCC No. 53908) |
| #55 | 07/22/88 | NTG | 50 | 10 | 10/12–11(leu$^-$) 10/12–24 (tyr$^-$) 10/12–24 (tyr$^-$) |
|  | 11/01/88 | NTG | 50 | 10 | 11/25–1 (tyr$^-$phe$^-$) 12/9–1 (tyr$^-$phe$^-$) (ATCC No. 55158) 11/26–1 (tyr$^-$trp$^-$) |
| NOA2 | 08/11/88 | NTG | 50 | 10 | 8/14–4 (hse$^-$) 8/16–5 (hse$^-$) 9/31–4 (phe$^-$) 9/31–4 (phe$^-$) |
|  | 11/01/88 | NTG | 50 | 10 | 11/10–12 (phe$^-$try$^-$) |

[1]NTG $\mu$g/ml; EMS $\mu$l/ml

Auxotrophic mutants of MGA3 and NOA2 can also readily be generated by exposure to ultraviolet light. Briefly, an auxotroph is grown to mid exponential phase (A600= 0.5–0.6) in a media containing methionine and threonine. The culture is then exposed to UV irradiation at 254 nm, preferably for a period of time less than one minute. Mutagenized cells were left to grow in the dark for 3 hours. Cells were then selected by growth in the presence of increasing amounts of s-aminoethyl-L-cysteine. Single colonies were isolated and plated onto plates lacking threonine and methionine to confirm auxotrophy.

A mutant of NOA2 8/16-5 (hse$^-$) generated by UV irradiation and which is resistant to 200 mg/l of s-2- aminoethyl-L-cysteine (AEC) was isolated. This mutant has been designated NOA2-L20#3-NA#29 and deposited with the ATCC on Mar. 17, 1993 and given Accession No. 55403. Several other mutants were also generated, some of which are described in the following Table:

TABLE V

Production of Auxotrophs

| Parent | Conditions | | New Mutant |
|---|---|---|---|
| | Agent | conc | |
| NOA2 | NTG | 50 μg/10 min | 8/16-5 (hse-) |
| NOA2 8/16-5 | UV, AEC | 500 μg/ml | L20NO3#NA30 (hse⁻) |
| NOA2 8/16-5 | UV, AEC | 200 μg/ml | L20NO3#NA29 (hse⁻) (ATCC No. ____) |
| L20NO3#NA29 | UV, AEC | 100 μg/ml | NA29#19 |
| | HL | 40 μg/ml | (hse⁻) |
| | ML | 10 μg/ml | |
| NA29#19 | UV, AEC | 200 μg/ml | NA19#50 |
| | HL | 80 μg/ml | (hse⁻) |
| | ML | 20 μg/ml | |
| NA19#50 | UV, AEC | 400 μg/ml | NA50#32 |
| | HL | 80 μg/ml | (hse⁻) |
| | ML | 40 μg/ml | |

UV = UV irradiation
AEC = S-2-aminoethyl-L-cysteine
HL = hydroxylysine
ML = methyllysine Auxotrophic mutants generated by chemical mutagenesis or UV irradiation can be exposed to additional mutagenic agents to generate additional auxotrophic mutants. Strain L20N03#NA29 is an auxotrophic mutant of strain NOA2 8/16-5 generated by UV irradiation. This strain was mutagenized with diepoxyoctane at 1000 μg/min. The cells were then washed and grown MV media containing 100 mg/l of 150 leucine and grown for 18 hours at 50° C.

The microorganisms were further selected in the presence of s-2-aminoethyl-L-cysteine (100 μg/ml), hydroxylysine (400 μg/ml) and methyllysine (10 μg/ml) and then surviving cells were treated with the mutagen diepoxyoctane again as described above. Surviving cells were again selected by growth in the presence of s-2-aminoethyl-L-cysteine (200 μg/ml) hydroxylysine (40 μg/ml) and methyllysine (10 μg/ml).

Surviving cells were further selected by growth in the presence of increasing concentrations of lysine or AEC. Cells surviving mutagenesis with diepoxyoctane and resistant to inhibition by AEC, HL and ML were grown on MV plates containing threonine (1 g/l) isoleucine (0.5 g/l) and methionine (0.25 g/l). Colonies were transferred to 2 ml MV medium containing 1 g/l threonine, 0.5 g/l isoleucine and 0.25 g/l methionine containing 20, 30, 40, 50 g/l lysine-HCl. Isolates that grew rapidly were selected and grown in the presence of 40 g/l and 50 g/l of lysine-HCl and 1 g/l AEC.

Rapidly growing isolates were grown in media containing 200 μg/ml threonine, isoleucine and methionine and examined for amino acid production. Following this protocol of mutagenesis and selection, 11 different isolates were identified and designated PO13-A5-2, PO13-A5-1, PO13-A5-4, PO13-3-8, PO13-3-26, PO13-8-17, PO13-8-18, PO13-8-19, PO13-10-32, PO13-10-33, and PO13-A5-3.

B. PROOF OF AUXOTROPHY

The amino acid requirements of each auxotrophic isolate was proven by its growth response to amino acids added to MV broth medium.

EXAMPLE 3

Analog Resistance

The lysine analog S-2-aminoethyl-L-cysteine (AEC) has been used effectively to select for lysine overproducing mutants from among auxotrophic and non-auxotrophic strains of MGA3 and NOA2. Mutants resistant to as much as 2 g/l of AEC have been produced in a stepwise manner (up to 5 steps so that AEC resistance of 2 g/l$^{-1}$ is achieved; at approximately 0.25 g/l$^{-1}$ increments) by plating mutagenized cells on MV media containing AEC and methionine, threonine, and isoleucine (250–500 mg/l). At each step media was incubated at 50° C. for 3 days. The resulting resistant isolates were challenged on media containing higher AEC concentrations until the desired level of resistance was reached or until an additional mutagenesis was required. There has been good correlation between increased AEC resistance and increased lysine production. The prototrophic strain MGA3 #55 was selected in the manner described above, was resistant to 2 g/l$^{-1}$ of AEC, and produced a 0.12 g/l$^{-1}$ of lysine. The amount of lysine produced was improved by the introduction of auxotrophic markers unrelated to the lysine pathway, e.g., 11/25-1 (try⁻ phe⁻) and 12/9-1 (tyr⁻ala⁻) which produced 0.6 and 0.8 gl$^{-1}$ amounts of lysine, respectively. Homoserine minus mutants such as 8/14-4 (hse⁻) produced about the same amount of lysine (0.6–0.9 g/l$^{-1}$) even without high AEC resistance; but the amount produced could be approximately doubled by selecting for mutants resistant to higher concentrations of AEC (600–1500 mg/l). Mutants can also be selected for resistance to other amino acid analogs such as hydroxylysine, methyllysine, and HNV (threonine analog) in a similar manner. See Example 2.

In a preferred version, selection of auxotrophs includes multiple selection steps in the presence of lysine and lysine analogs. Homoserine auxotrophs of *Bacillus methanolicus* strains MGA3 or NOA2 obtained after mutagenesis were typically first selected by resistance to AEC as described above. Additional selection step or steps were optionally employed involving growth of the auxotroph in the presence of AEC and hydroxylysine and methyllysine. In between steps, isolates were screened for lysine production as described in Schendel et al., *Appl. Env. Microbiol.*, 56: 963 (1990), which is hereby incorporated by reference. The isolates that produced the highest amounts of lysine were then grown in the presence of increasing concentrations of lysine-HCl ranging from 20–50 g/l. Isolates growing rapidly in the presence of lysine-HCl were grown in the presence of threonine, methionine and isoleucine and tested for lysine production. Optionally, isolates were further selected by growth in the presence of the threonine analog HNV (1 μg/ml). For example, strain L-20-1-3 is an auxotrophic strain derived from NOA2 8/16-5 by selection with 600 μg/ml AEC followed by growth in 20 g/l L-lysine and further selection by growth in the presence of threonine analog HNV.

EXAMPLE 4

Amino Acid Overproduction

Lysine and other amino acids were determined in culture supernatants by the acidic ninhydrin assay method, described in Work, *J. Biochem.*, 67: 416–423 (1957), incorporated by reference herein. The ninhydrin reagent was prepared by combining 64 ml of glacial acetic acid, 16 ml of 0.6M phosphoric acid, and 1 g of ninhydrin (Sigma #N-4876). Culture samples were centrifuged for 2 minutes at high speed in an Epindorph centrifuge. Culture supernatant (0.05 ml) was combined with ninhydrin reagent (0.55 ml) in 5 ml screw capped Pyrex tubes. Standard solutions of amino acids were treated the same way. The tubes were heated for 1 hour in a 100° C. water bath and glacial acetic acid (1.4 ml) was added to the cooled tubes. Absorbance was read at 440 nm on a Beckmann DU-70 spectrophotometer that computed the amino acid concentration through regression analysis. The assay results were very linear and repeatable from day to day.

Alternatively, amino acids were determined by HPLC using pre-column derivatization with o-phtalaldehyde (OPA) and fluorescence detection of the OPA-amino acid derivative. Culture supernatants were diluted 50–500 fold with methanol, and then centrifuged for 2–5 minutes at high speed to remove any precipitated protein. The sample (25 $\mu$L) was then mixed with o-phtalaldehyde (Pierce #26015) (50 $\mu$ML), then injected onto a 5$\mu$ particle size C-18 reverse phase column (Alltech #28066). Separation of the OPA amino acids was carried out using a flow rate of 1 mL/min and a non-linear gradient from 10–50% acetonitrile in 50 mM potassium phosphate (pH 6.8).

Shake Flask Screening Method

For screening of potential lysine or other amino acid producers, mutants of MGA3 or NOA2 were grown on medium containing 10 g/L $K_2HPO_4$, 32 g/L $(NH_4)_2SO_4$, 10 g/L $CaCO_3$, 0.2 g/L $MgCl_2.6H_2O$, 20 g/L methanol, trace metals at the concentration described below, vitamins (biotin, 50 $\mu$g/L and $B_{12}$ 10 $\mu$g/L), and 200 mg/L of any amino acids required for growth. The strains were cultured in 25 mL of the above medium in a 250 mL baffled shake flask covered with milk filter disks, and a piece of 2 mil teflon membrane to reduce methanol evaporation. The cultures were started using a 1–4% inoculum and grown at 50° C. in an air shaker with a revolution rate of 300 rpm. The concentration of methanol was determined every 12 hours by removing a sample, separating the cells by centrifugation, and injecting the supernatant into a gas chromatograph. More methanol was added to the flask if the concentration dropped below 200 mM. Experiments were usually carried out for a period of 24–48 hours. Lysine formation was determined by either ninhydrin or HPLC. The results from screening several mutants are shown in Table VI. These result correlated well with the production of lysine in 5 liter stirred tank reactor with a methanol feeding.

TABLE VI

| Strain | Shake Flask Lysine (g/L) | Reactor Lysine (g/L) |
| --- | --- | --- |
| NOA2 8/14-4 | 0.96 | 2.2 |
| NOA2 R2 | 0.60 | 0.50 |
| NOA2 8/16-5 #1 | 2.6 | ND[1] |
| NOA2 8/16-5 #3 | 2.8 | 4.5 |
| Gr 7/30-15 #1 | 4.1 | 4.0 |
| Gr 7/30-15 #2 | 7.0 | 7.0 |
| MGA3 11/25-1 | 0.58 | ND[1] |
| MGA3 12/9-1 | 0.11 | 0.8 |
| NOA2 8/16-5 | 7.8 | 8.0 |

ND – not determined

Lysine Production in a Stirred Reactor

Lysine was over produced in the aerated stirred reactor by culturing the appropriate mutant strain of the present invention using either sulfate or phosphate limited minimal salts media. When sulfate limitation was used, ammonium chloride replaced the ammonium sulfate, and all trace metals were used as their chloride salts. The sulfate required for growth was supplied as potassium sulfate. The amino acids required for growth of the lysine producers were supplied at the concentrations necessary to reach the desired cell densities by feeding either pure amino acids or amino acid hydrolysates. Cells can be cultured with growth rates from 0.5–1 $\mu$max using the following concentration ranges of nutrients.: ammonium sulfate from 20–500 mM, sulfate from 0.1–500 mM, methanol from 20–800 mM, phosphate from 10–125 mM, magnesium from 0.5–20 mM, manganese from 2–100 $\mu$M, iron from 10–800 $\mu$M, calcium from 0.1–1.5 mM, chloride from 0–80 mM, zinc from 1–20 $\mu$M, cobalt from 0.1–20 $\mu$M, copper from 0.1–20 $\mu$M, molybdate from 0.2–40 $\mu$M, borate from 0.4–8 $\mu$M, vitamin $B_{12}$ from 0.5 $\mu$g/l$^{-1}$–1 mg/l$^{-1}$, and biotin from 20 $\mu$g/l$^{-1}$–20 mg/l$^{-1}$. The pH of the reactor was maintained at 7.1 by the addition of ammonium hydroxide. The dissolved oxygen concentration was maintained at a level of 10% by adjusting either the agitation rate, the aeration rate, or by the addition of pure oxygen. Foaming was controlled by the automatic addition of a silicon based antifoam (SAG-471). The methanol concentration was monitored by gas chromatography, and maintained between 50–600 mM by periodic addition of methanol to the reactor. Lysine production was primarily non-growth associated, and excess threonine was shown to inhibit lysine formation. The amount of lysine formed was essentially the same when either phosphate or sulfate limitation was used. When the organism Gr 7/30-15 #1 was cultivated in the reactor under sulfate limitation, a total of 4.0 g/l$^{-1}$ of cell dry weight produced 7.0 g/l$^{-1}$ of lysine during the 40 hour cultivation.

EXAMPLE 5

A Method to Obtain Growth to High Cell Density

Figure 5:
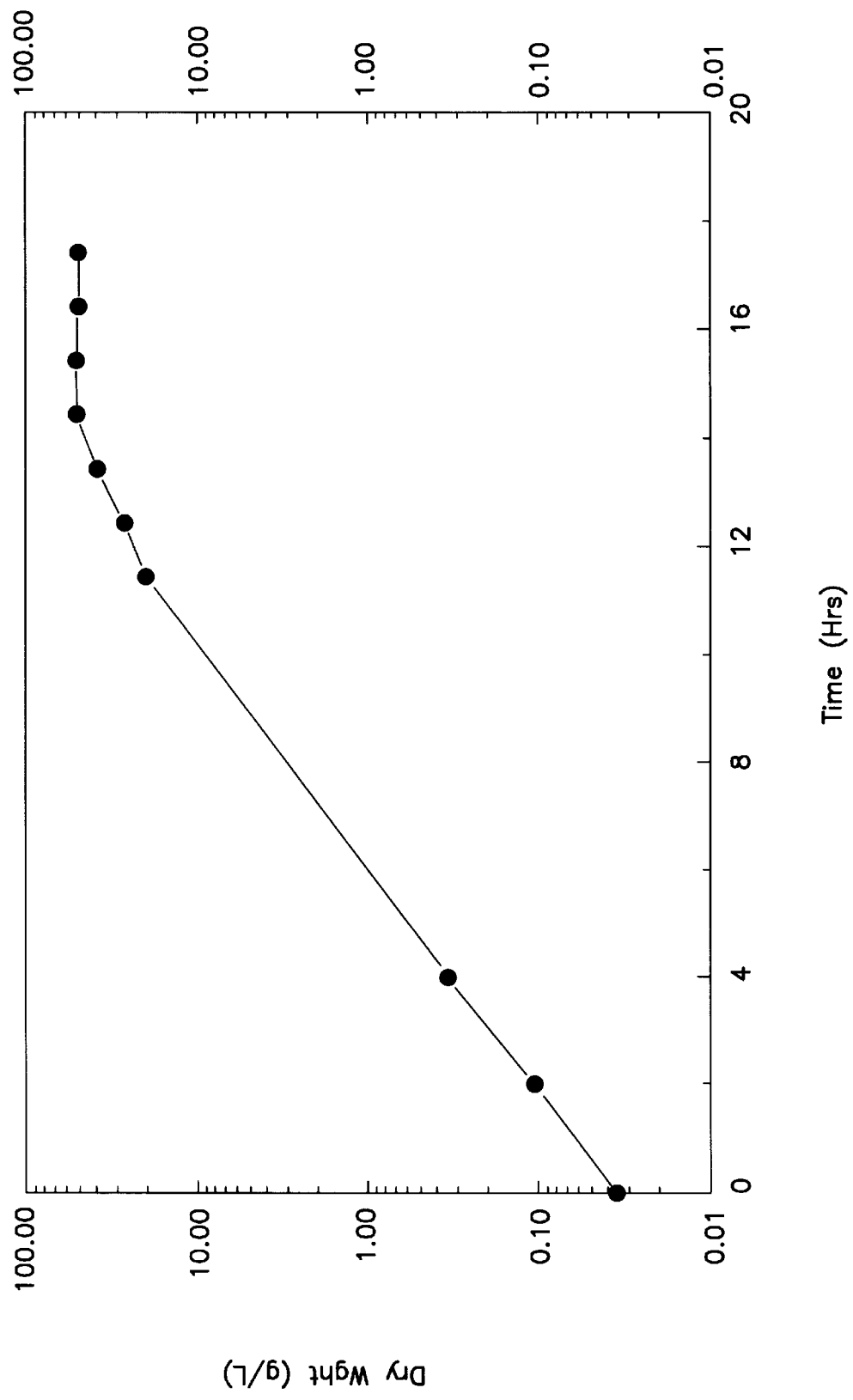
FIG. 5 shows MGA3 growth to high cell density under semi-continuous or fed-batch conditions.

The growth of MGA3 to high cell density has been accomplished by using the following medium and nutrient feeding systems. The medium contained 3.09 g/l$^{-1}$ $K_2HPO_4$, 0.9 g/l$^{-1}$ $NaH_2PO_4$, 2 g/l$^{-1}$ $(NH_4)_2SO_4$, 20 mg/l$^{-1}$ biotin, 0.2 g/l$^{-1}$ $MgCl_2.6H_2O$, 1 mg/l$^{-1}$ vitamin $B_{12}$, 3.98 mg/l$^{-1}$ $FeCl_2.4H_2O$, 7.36 mg/l$^{-1}$ $CaCl_2.2H_2O$, 9.9 mg/l$^{-1}$ $MnCl_2.4H_2O$, 136 $\mu$g/L $ZnCl_2$, 54.4 $\mu$g/L $CuCl_2.2H_2O$, 80.4 $\mu$g.1$^{-1}$ $CoCl_2.2H_2O$, 96.8 $\mu$g/l$^{-1}$ $Na_2MoO_4.2H_2O$, 59.6 $\mu$g/l$^{-1}$ $H_3BO_3$, 3.2 g/l$^{-1}$ methanol, and 250 mg/l$^{-1}$ yeast extract. The concentrations of the nutrients could vary as described in Example 4. Cultivation of the cells was carried out at 50° C. in a 14 liter fermentor with an 11 liter working volume. The agitation rate was varied from 900–1500 rpm. The pH was maintained at 6.3–7.1 by addition of 8N ammonium hydroxide or gaseous ammonia. The ammonium hydroxide also served as a nitrogen source. Phosphate, magnesium, and calcium levels were maintained by automatically feeding a solution of 10:1:0.1 phosphate:magnesium:calcium (1M $KH_2PO_4$.0.1M $MgCl_2.6H_2O$, 0.01M $CaCl_2.2H_2O$). Feeding of the phosphate/magnesium/calcium mix was carried our by connecting the pump to the pH controller, so that the phosphate/magnesium/calcium solution would be fed whenever the ammonium hydroxide or gaseous ammonia was added to adjust the pH. The rate of the ammonium hydroxide (8N) to phosphate-magnesium-calcium feed (1M phosphate, 0.1M magnesium, 0.01 calcium) was adjusted to give a ratio of 1:2. This maintained the proper balance of nitrogen, phosphate, magnesium, and calcium. The aeration rate was varied from 0.5 to 2 vvm. The dissolved oxygen concentration was monitored by using a galvanic probe, and the level of dissolved oxygen was maintained at 30% by using pure oxygen-enriched aeration. The amount of pure oxygen used was monitored and controlled by using a mass flow controller interfaced to the dissolved oxygen probe. Foaming was controlled using a liquid level controller by the automatic addition of a silicon based anti-foam, (SAG-471). Exhaust gasses (carbon dioxide, oxygen, nitrogen, argon, methanol, ammonia, and water) were monitored by mass spectrometry. The methanol level was continuously monitored by using an on-line methanol sensor consisting of the silicon tubing probe described by Tsao and Austin, *Control of Methanol Concentration Using an On-ine Methanol Sensor*, American Chemical Society National Meeting, Toronto, Ontario, Canada (June, 1988), and a hydrocarbon sensor (TGS A22, Figaro USA Inc., Wilmette, Ill.). The signal from the hydrocarbon sensor was used to automatically operate the methanol feed pump (Watson-Marlow) by use of a proportional controller. The amount of methanol fed to the culture was monitored using a load cell. The methanol also contained the required trace metals in the following concentrations: 1.09 g/l$^{-1}$ FeSO$_4$.7H$_2$O, 0.39 g/l$^{-1}$ MnCl$_2$.4H$_2$O, 22 mg/l$^{-1}$ ZnSO$_4$.7H$_2$O, 19 mg/l$^{-1}$ CoCl$_2$.6H$_2$O, 19 mg/l$^{-1}$ Na$_2$MoO$_4$.2H$_2$O, and 19 mg/l$^{-1}$ CuSO$_4$.5H$_2$O. Using this media and the feeding strategies described above, the organism could be grown to cell densities of 50 g/l$^{-1}$ cell dry weight (FIG. 5).

EXAMPLE 6

Production of Glutamate and Other Amino Acids

Cultivation of mutants under limiting culture conditions can result in production of one or more amino acids. Mutants prepared as described in Example 2, including those generated by UV irradiation, coproduce both glutamate and lysine. After 30 hours of cultivation, the reactor typically contained about 20–30 gm/l cell dry weight, about 10–15 gm/l glutamate, and about 10–30 gm/l lysine.

Mutant NA#29 was grown in an 14 liter fed-batch fermentations under conditions which limited the supply of amino acids methionine and threonine. The ratio of amino acids produced by the mutants can be altered by controlled feeding with threonine. Automated threonine feeding at controlled levels coupled to methanol uptake can result in cell mass accumulation up to 25 g/l cell dry weight with lysine yields up to 28 g/l. Other threonine feeding conditions can lead to the selective enhancement of production of a different amino acid, such as glutamate.

Forty microliters of culture of NA#29 frozen at −80° C. in 30% glycerol were used to inoculate 10 ml of MY media. After 7 hours of incubation with shaking at 50° C., 40 μl were transferred to 10 ml of MS media and incubated for 12 hours. Six ml were transferred to 300 ml of MS medium and incubated for 8 hours. MS media (200 ml) was then added to the flask and incubation was continued for approximately 5 hours. All the cultures described above were incubated on a rotary shaker at 50° C.

The 500 ml culture from the final shake flask was used to inoculate a 14 liter reactor when the absorbance of the culture at 600 nm was 1.315. The bioreactor was operated so that the concentrations of threonine, methionine and phosphate would become growth rate limiting when the cell density reached 6–10 grams per liter of cell dry weight. The feeding of threonine and methionine was adjusted manually and stopped at 15 hours. The final cell density was about 20 grams dry weight per liter.

The methanol concentration was monitored in the exhaust gas by a quadrapole mass spectrometer (Questar) and in the liquid phase using a silicone tubing dissolved methanol probe with a Figero TGS 822 hydrocarbon gas sensor. PID control using a Micromac 5000 computer was used to control methanol feed rates and to maintain a dissolved methanol concentration of 100 mM.

Samples were removed from the reactor in order to maintain a culture volume of 11 liters. The pH of the culture was maintained at about pH 6.3–7.1 by the addition of 8M ammonium hydroxide or anhydrous ammonia. Dissolved oxygen was maintained at 15% of air saturation by use of a PID controller and oxygen-enriched aeration.

Figure 6:
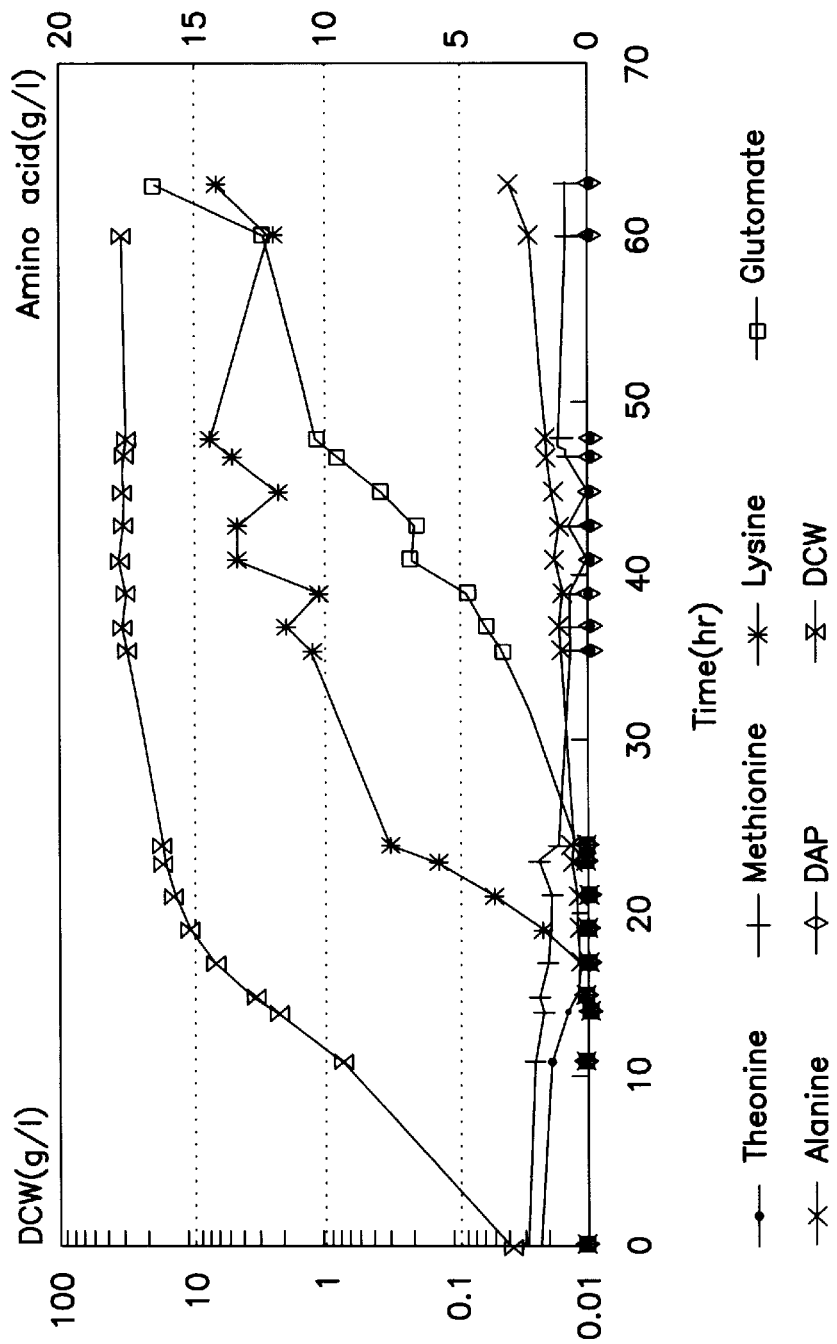
FIG. 6 shows simultaneous production of glutamate and lysine by an auxotrophic bacteria of the present invention (NA#29).

FIG. 6 shows the growth of strain NA#29 and the production or consumption of amino acids. Lysine production began at the beginning of the stationary phase of growth and continued until approximately 50 hours. The final concentration of lysine was 14 grams per liter. Glutamic acid was produced between 22 and 65 hours during the fermentation. The highest rates of glutamate production under these cell culture conditions occurred when the rate of lysine production had decreased. The final glutamate concentration was 17 grams per liter.

Figure 7:
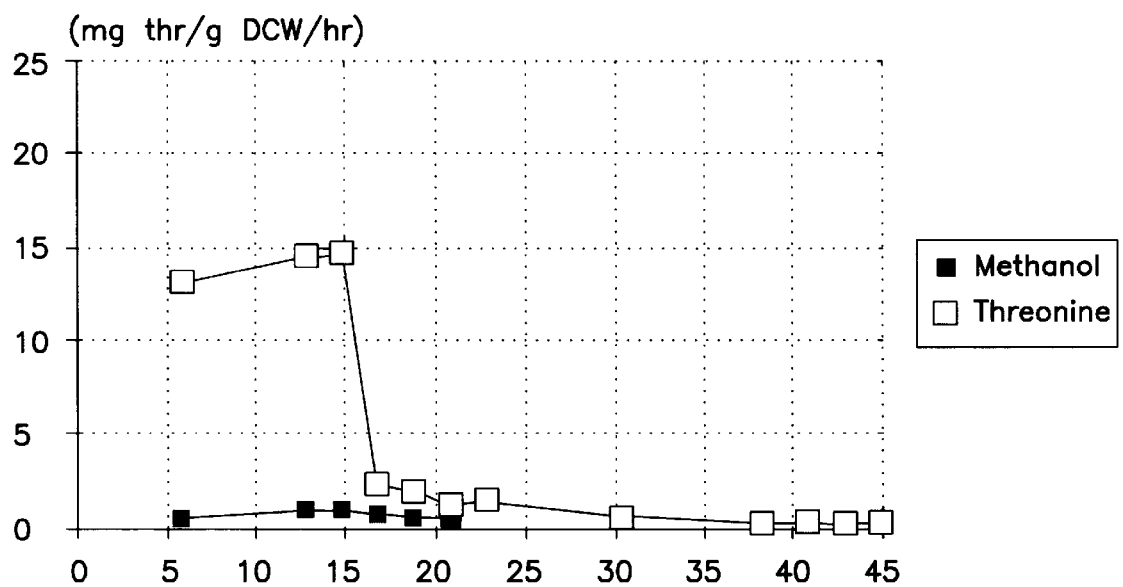
FIG. 7 shows the rates of methanol consumption and threonine feeding in fed-batch culture shown in FIG. 8.

In another example, a mutant of *Bacillus methanolicus* strain NOA2 designated Bacillus L-20-1-3 obtained as described in Example III was grown under similar 11 liter fed-batch conditions as described previously. Threonine was fed at rates shown in FIG. 7. Threonine was fed initially at a 5× concentration of about 15 mg/g DCW/hr until 15 hours and then threonine was dropped to about 1× concentration of about 1–3 mg/g DCW/hr. As the cells began to require more threonine, the amount of threonine being fed to the culture was decreased 5-fold. Methanol was fed and consumed at a constant rate and did not accumulate.

Figure 8:
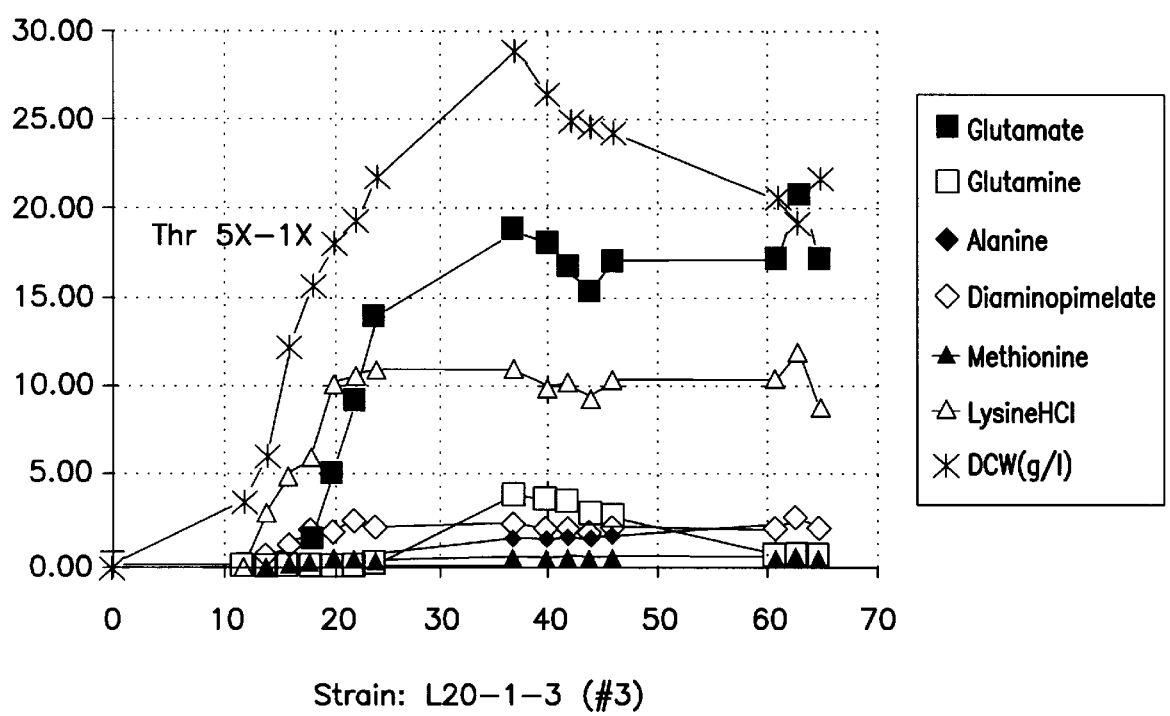
FIG. 8 shows co-production of glutamate and lysine by an auxotrophic bacteria strain L20-1-3.

The results shown in FIG. 8 indicate that growth of this mutant under limiting conditions of threonine resulted in the production of both glutamate and lysine. Glutamate was produced at a level of about 15–20 gm/l and lysine was produced at a level of about 10 gm/l. After about 20 hours of growth, the cell dry weight yields were between 20–30 gm/l. The glutamate and lysine began to be produced shortly after threonine feeding levels were dropped 5-fold. In this case, both glutamate and lysine production increased simultaneously.

Figure 10:
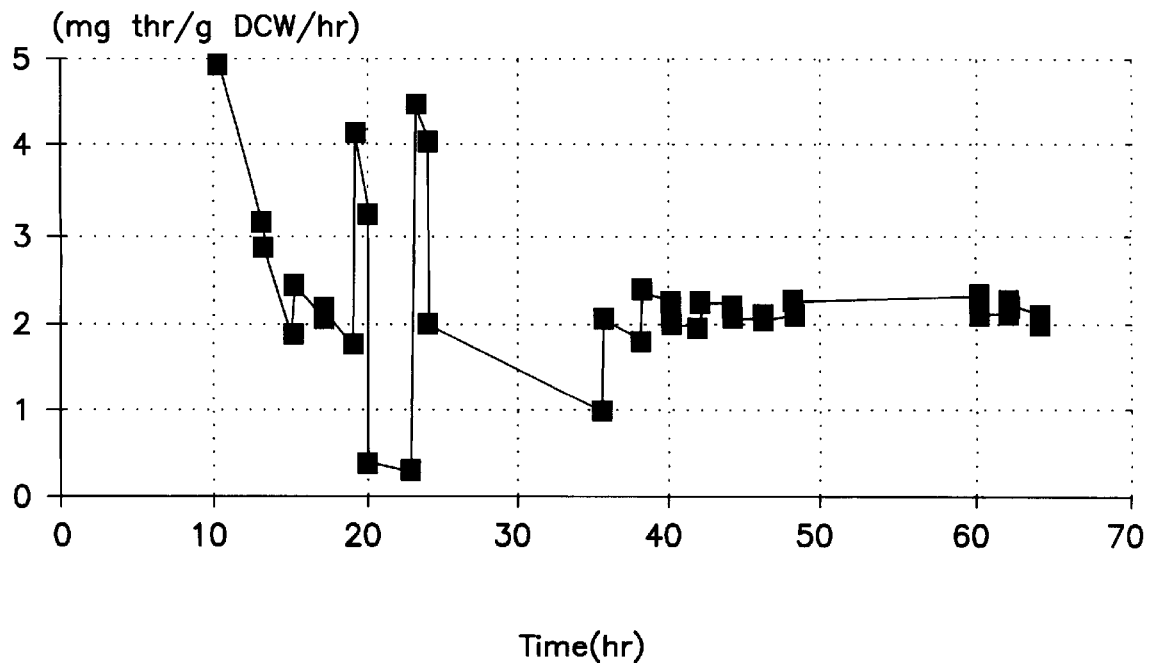
FIG. 10 shows the threonine feeding of the fed-batch culture shown in FIG. 11.

When threonine feeding conditions were altered, production of amino acids by the auxotrophs of the invention can be altered. Strain # 13A5-2 is an auxotrophic mutant obtained as described in Example 2 was grown under similar 11 liter fed batch conditions. Threonine was fed as shown in FIG. 10. Threonine was fed at a constant growth limiting concentration of about 2 mg threonine/g DCW/hour for the period.

Figure 11:
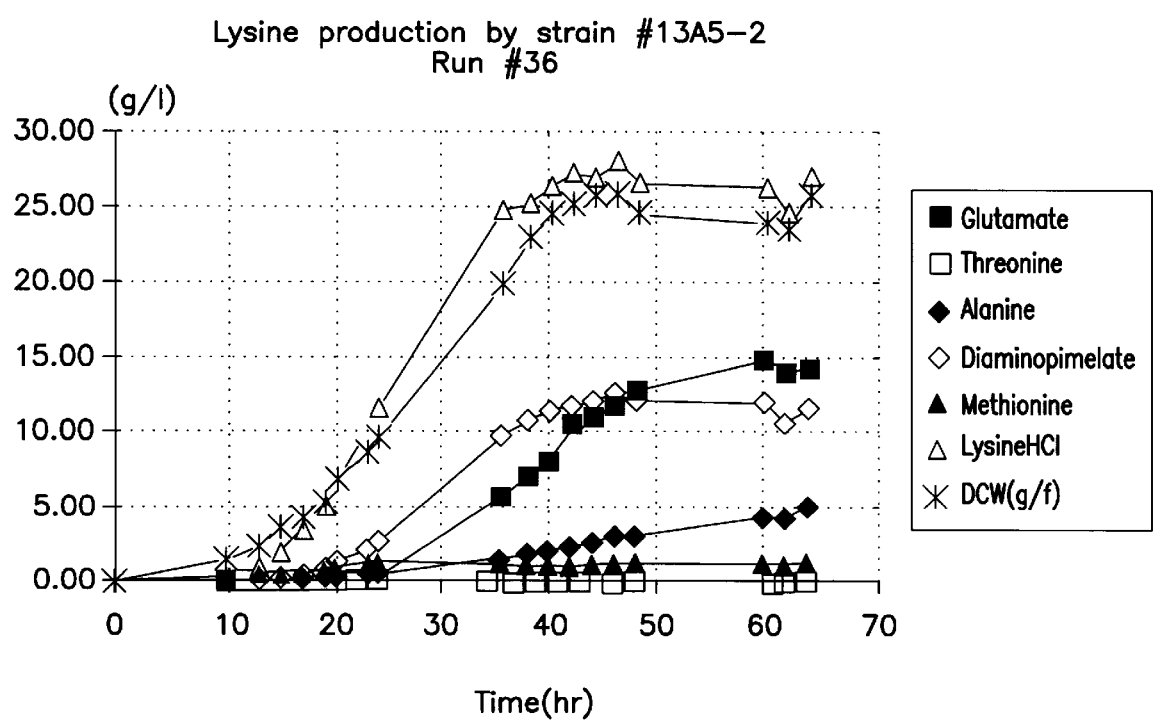
FIG. 11 shows coproduction of glutamate and lysine by strain #13 A5-2.

The results shown in FIG. 11 indicate that growth of this mutant under limiting conditions of threonine resulted in coproduction of lysine and glutamate. Glutamate was produced at 10–15 g/l after about 40 hours. Lysine was produced at 25–28 g/l after 30 hours. After 30 hours of growth, the cell dry weight yields were about 25 g/l. The lysine began to be produced shortly after threonine limitation and glutamate production was seen later.

These results indicate that homoserine auxotrophs of *Bacillus methanolicus* strain NOA2 selected for resistance to lysine analogs produce glutamic acid, aspartic acid, and diaminopimelic acid in substantial amounts when deprived of the required amino acids threonine and methionine. Different mutants produce different amino acids, and the culture conditions can be manipulated to favor production of one amino acid over another by controlled feeding of threonine. Auxotrophic *Bacillus methanolicus* mutants can be grown in fed-batch conditions and can be manipulated by threonine limiting conditions to overproduce two or more amino acids.

All publications and patent applications in this specification are indicative of the level of ordinary skill in the art to which this invention pertains. All publications and patent applications are herein incorporated by reference to the same extent as if each individual publication or patent application was specifically and individually indicated by reference.

It will be apparent to one of ordinary skill in the art that many changes and modifications can be made in the invention without departing from the spirit or scope of the appended claims.

What is claimed is:

1. A method for producing glutamic acid which comprises
(a) culturing a biologically pure culture of a ribulose-monophosphate-pathway-utilizing, auxotrophic mutant of a strain of *Bacillus methanolicus* in a nutrient medium comprising vitamin $B_{12}$ and wherein methanol is a primary carbon source, at a temperature of about 35° C. to about 60° C. until glutamic acid is produced at a concentration of at least about 5 g/l, wherein said auxotrophic mutant is obtained from a parent strain selected from the group consisting of *Bacillus methanolicus* MGA3, an environmental isolate having all the identifying characteristics of *Bacillus methanolicus* MGA3, a stable morphological mutant of *Bucillus methanolicus* MGA3, and a stable morphological mutant of an environmental isolate having all the identifying characteristics of *Bacillus methanolicus* MGA3, wherein the identifying characteristics of *Bacillus methanolicus* MGA3 are: rod-shape, non-motile, Gram positive, spores at a suberminal to central position, growth at 35° C. to 60° C. optimum growth at 55° C., growth on methanol, and a G/C content of 44% to 52%; and (b) recovering said at least about 5 g/l of glutamic acid from the nutient medium.

2. A method according to claim 1, wherein the auxotrophic mutant is a homoserine auxotroph.

3. A method according to claim 1, wherein the auxotrophic mutant is resistant to growth inhibition by a lysine analog selected from the group consisting of s-2-aminoethyl-L-cysteine, hydroxylysine, methyllysine, and mixtures thereof.

4. A method according to claim 1, wherein the step of culturing further comprises limiting the amount threonine present in the nutrient media.

5. A method according to claim 4, wherein threonine is provided at 0.04 gm/l/hr to 0.3 gm/l/hr.

6. A method according to claim 1, wherein the auxotroph is capable of excreting an amino acid selected from the group consisting of alanine, aspartic acid, lysine, and mixtures thereof.

7. A method according to claim 6, wherein the auxotroph is capable of excreting lysine at a concentration of at least about 5 gm/l.

8. A method according to claim 1, wherein in the step of culturing, the pH is maintained at a pH of about 6.3 to 7.2.

9. A method according to claim 1 wherein the auxotrophic mutant has all the identifying characteristics of ATCC No. 55403.

* * * * *